(12) United States Patent
Murray et al.

(10) Patent No.: US 12,383,348 B2
(45) Date of Patent: Aug. 12, 2025

(54) NAVIGATED FORCE SENSING INSTRUMENTS

(71) Applicant: GLOBUS MEDICAL, INC., Audubon, PA (US)

(72) Inventors: Patrick Murray, Collegeville, PA (US); David Leff, Philadelphia, PA (US); Albert Hill, Richboro, PA (US); John LaColla, West Chester, PA (US); Shruthi Muralidharan, Philadelphia, PA (US); Jeff Nichols, Medford, NJ (US); Amir Soltanianzadeh, King of Prussia, PA (US)

(73) Assignee: Globus Medical Inc., Audubon, PA (US)

( * ) Notice: Subject to any disclaimer, the term of this patent is extended or adjusted under 35 U.S.C. 154(b) by 304 days.

(21) Appl. No.: 18/300,589

(22) Filed: Apr. 14, 2023

(65) Prior Publication Data

US 2024/0341854 A1 Oct. 17, 2024

(51) Int. Cl.
*A61B 34/20* (2016.01)
*A61B 17/70* (2006.01)
*A61B 90/00* (2016.01)

(52) U.S. Cl.
CPC .......... *A61B 34/20* (2016.02); *A61B 17/7074* (2013.01); *A61B 90/06* (2016.02); *A61B 2034/2051* (2016.02); *A61B 2090/064* (2016.02); *A61B 2090/397* (2016.02)

(58) Field of Classification Search
CPC ..... A61B 34/20; A61B 90/06; A61B 17/7074; A61B 2034/2051; A61B 2090/064; A61B 2090/397
See application file for complete search history.

(56) References Cited

U.S. PATENT DOCUMENTS

| | | | | |
|---|---|---|---|---|
| 6,716,218 B2 * | 4/2004 | Holmes | .............. | A61B 17/8866 606/105 |
| 10,194,995 B2 * | 2/2019 | Neo | ........................ | A61B 34/20 |
| 10,368,917 B2 * | 8/2019 | Mishra | ............... | A61B 17/7032 |
| 10,736,671 B2 * | 8/2020 | Leff | .................... | A61B 17/7086 |
| 10,869,699 B2 * | 12/2020 | Leff | ....................... | A61B 17/705 |

FOREIGN PATENT DOCUMENTS

EP 3936075 A2 * 1/2022 ............. A61B 34/10

* cited by examiner

*Primary Examiner* — Kevin T Truong
*Assistant Examiner* — Diana Jones

(57) ABSTRACT

Navigated force sensing instrument, systems, and methods. The navigated force sensing instruments may be used for applying forces to correct the spine, for example, in compression, distraction, reduction, and/or derotation. The trackable instrument includes markers viewable and trackable by a navigation system, including rigid and movable markers. The trackable instrument includes a flexible portion located between the rigid and movable markers. When a surgical task is performed, the markers indicate the amount of force applied to the instrument and/or a stiffness of the spine.

20 Claims, 20 Drawing Sheets

NAVIGATED FORCE SENSING INSTRUMENTS

FIELD OF THE INVENTION

The present disclosure generally relates to navigated force sensing instruments and methods of implementing navigation and/or electromechanical control of instruments for a medical procedure, such as correcting a spinal deformity.

BACKGROUND OF THE INVENTION

Many types of spinal irregularities cause pain, limit range of motion, or injure the nervous system within the spinal column. These irregularities may result from, without limitation, trauma, tumor, disc degeneration, disease, and deformity. Often, these irregularities are treated by immobilizing a portion of the spine, for example, by affixing screws to the vertebrae and connecting the screws to an elongate spinal rod that stabilizes the spine.

During spine surgery, the surgeon may apply forces to correct the spine. The surgeon may manually apply the corrective forces to the grip or handle of an instrument. The corrective forces, displacement, and rotation of the spine may be controlled by the surgeon with tactile feedback and visualization of the posterior anatomical elements. X-ray imaging may be used to confirm that sufficient correction has been achieved and various neurological tests may be performed to ensure that the patient is neurologically stable and that the spinal cord has not been compromised.

The introduction of robotics into spine surgery has enhanced safety and improved efficiency for surgeons during deformity correction. Imaging and navigation technologies combined with robotics have enabled surgeons to receive real time feedback on clinically significant parameters that previously could not be assessed intraoperatively. There exists a need, however, for devices and methods of improving feedback and information to the surgeons. Devices and methods integrating robotic, imaging, and/or navigation technologies into spinal deformity correction procedures may further improve the safety, efficacy, reliability, and/or repeatability of correction maneuvers during deformity surgery.

SUMMARY OF THE INVENTION

To meet this and other needs, navigated instruments, systems, and methods are provided. In particular, navigated instruments may be tracked during spinal procedures, for example, when applying forces to correct the spine in compression, distraction, reduction, and/or derotation. Force sensing instruments, which employ optical tracking methods, may be used to measure the deflections of load-bearing portions of the instruments. Knowledge of the stiffnesses of these portions of these instruments may be employed to calculate the force applied to the instrument. The navigation features may be used to track the location of the instrument and implants rigidly attached to the instruments. The force measuring instruments may also be used to characterize the stiffness of the spine by measuring the navigated displacements of the spine resulting from applied forces. In addition, devices and methods of implementing navigation and electromechanical control of instruments for correcting a spinal deformity are provided. These devices may interface with a pedicle screw system, which permits transmission of corrective forces to the vertebrae during the operation and, once locked to a spinal rod, rigidly holds the spine in the corrected position as the vertebrae fuse post-operatively.

According to one embodiment, a trackable instrument for correcting a spinal deformity includes a body having a distal portion configured to perform a surgical task and a proximal portion configured to be manipulated by a user, a plurality of markers configured to be tracked by a navigation system including a rigid marker and a movable marker attached to the body, a flexible portion located along the body, and the flexible portion is positioned between the rigid marker and the movable marker. When the surgical task is performed, the plurality of markers indicate an amount of force applied to the instrument.

The trackable instrument may include one or more of the following features. The instrument may be further configured to characterize a stiffness of a spine by measuring navigated displacements of the spine resulting from applied forces by the instrument. The surgical task may include compression, distraction, reduction, and/or derotation of the spine. The flexible portion may have a known stiffness. Relative motion of the movable marker relative to the rigid marker may result from the known stiffness of the flexible portion, and the relative motion may be measurable by the navigation system. The flexible portion may include one or more relief cuts, a reduced segment having a reduced width, and/or a flexible material section. The flexible portion may include one or more relief cuts having linear or helical cuts. The flexible portion may include linear relief cuts, a decreased width, and a helical cut, thereby resulting in decreased stiffnesses in different directions due to varying orientations of removed material.

According to one embodiment, a system for correcting a spinal deformity includes a navigation system including an infrared signal based position recognition system, and a trackable instrument having a plurality of markers viewable and trackable by the navigation system. The plurality of markers includes a rigid marker and a movable marker attached to the instrument. The trackable instrument includes a flexible portion having a known stiffness, and the flexible portion is located between the rigid marker and the movable marker. Relative motion of the movable marker relative to the rigid marker results from the stiffness of the flexible portion, and the relative motion is measurable by the navigation system. The trackable instrument may be a compressor, distractor, reducer, derotator, or rib pusher, for example.

According to one embodiment, the trackable instrument is a compressor or distractor having a first pivoting arm and an opposed second pivoting arm interconnected at a center pivot pin. The first and second pivoting arms each define a handle. The flexible portion is defined in one of the handles above the pivot pin. The rigid marker is affixed to a rigid segment of the first or second pivoting arm, and the movable marker is affixed to one handle on an opposite side of the flexible portion. For example, a first rigid marker may be attached to the first pivoting arm below the center pivot pin, a second rigid marker is attached to the second pivoting arm above the center pivot pin on one side of the instrument, and the movable marker is attached to the handle via a lever arm on the opposite side of the instrument.

According to another embodiment, the trackable instrument is a rod link reducer having a manipulator rod and a handle. The flexible portion is defined into the manipulator rod. A proximal array including the movable marker is located proximally and a distal array including a rigid marker is located distally along the manipulator rod. The flexible portion separates the distal array from the proximal array. The flexible portion may include linear relief cuts, a decreased width, and a helical cut positioned between the two arrays.

According to another embodiment, the trackable instrument is a rib pusher having a body handle defining a hollow interior, a plunger having a piston received in one end of the body handle, and a spring located in the body handle. The rigid marker is located on the body handle, and the movable marker is located on the plunger. The rib pusher may be used to apply a force on the ribs. The location of the applied force may be navigated. The amount of applied force may be calculated, and the amount of the spine's stiffness may be assessed by the surgeon.

According to another embodiment, the trackable instrument is a reducer having a body, a pair of engagement tabs attached to the body, and a central pusher threaded through the body. The rigid marker is located on the body, and the movable marker is located on the engagement tab. Each engagement tab may have a proximal section and a distal section that terminates at a free end configured to engage a modular tulip head. The engagement tab is attached to the body at a connecting portion adjacent to a flexure. When tension is applied to the engagement tab during reduction or derotation, the proximal section acts as an extended moment arm, and extends off of the flexure to magnify displacement of the movable marker.

According to yet another embodiment, a method of correcting a spinal deformity includes one or more of the following steps: (1) applying a force to a spine with a trackable instrument, the trackable instrument having a plurality of markers viewable and trackable by a navigation system, the plurality of markers including a rigid marker and a movable marker attached to the instrument, the trackable instrument includes a flexible portion located between the rigid marker and the movable marker, the flexible portion including one or more relief cuts, a reduced segment having a reduced width, and/or a flexible material section; and (2) monitoring movement of the rigid and movable markers to determine the force applied to the instrument. The method may further include determining a stiffness of the spine along a single motion or multi-motion spine segment. The method may further include applying torque to the spine segment to adjust an angle of the spine segment. The force may include applying torque in three directions. The movable marker may be configured to measure the applied torques at varying resolutions and magnitudes based on the amount of torque applied in each direction. The method may also include attaching navigated screw extenders to bone fasteners installed in vertebrae, and monitoring the screw extenders to determine movement of the vertebrae.

According to yet another embodiment, a kit may include a plurality of instruments or components thereof of different types and configurations. The kit may further include one or more implants, such as bone screws including screw extenders, spinal rods, or other devices suitable for correcting a spinal deformity.

BRIEF DESCRIPTION OF THE DRAWINGS

The present embodiments will become more fully understood from the detailed description and the accompanying drawings, wherein.

DETAILED DESCRIPTION

Embodiments of the disclosure are generally directed to navigated force sensing instruments, systems, and methods. In particular, navigated instruments may be tracked during spinal procedures, for example, when applying forces to correct the spine in compression, distraction, reduction, and/or derotation. Navigated force sensing instruments may be used to measure the deflections of load-bearing portions of the instrument. Knowledge of the stiffnesses of these portions of the instruments may be employed to calculate the force applied to the instrument. The navigated force measuring instruments may also be used to characterize the stiffness of the spine by measuring the navigated displacements of the spine resulting from applied forces. Although generally described for use with correcting a spinal deformity, it will be readily appreciated by those skilled in the art that the instruments may be employed in any number of suitable orthopedic approaches or other procedures.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments or modifications thereof are contemplated as falling within the scope of this disclosure and equivalents thereto.

Figure 1:
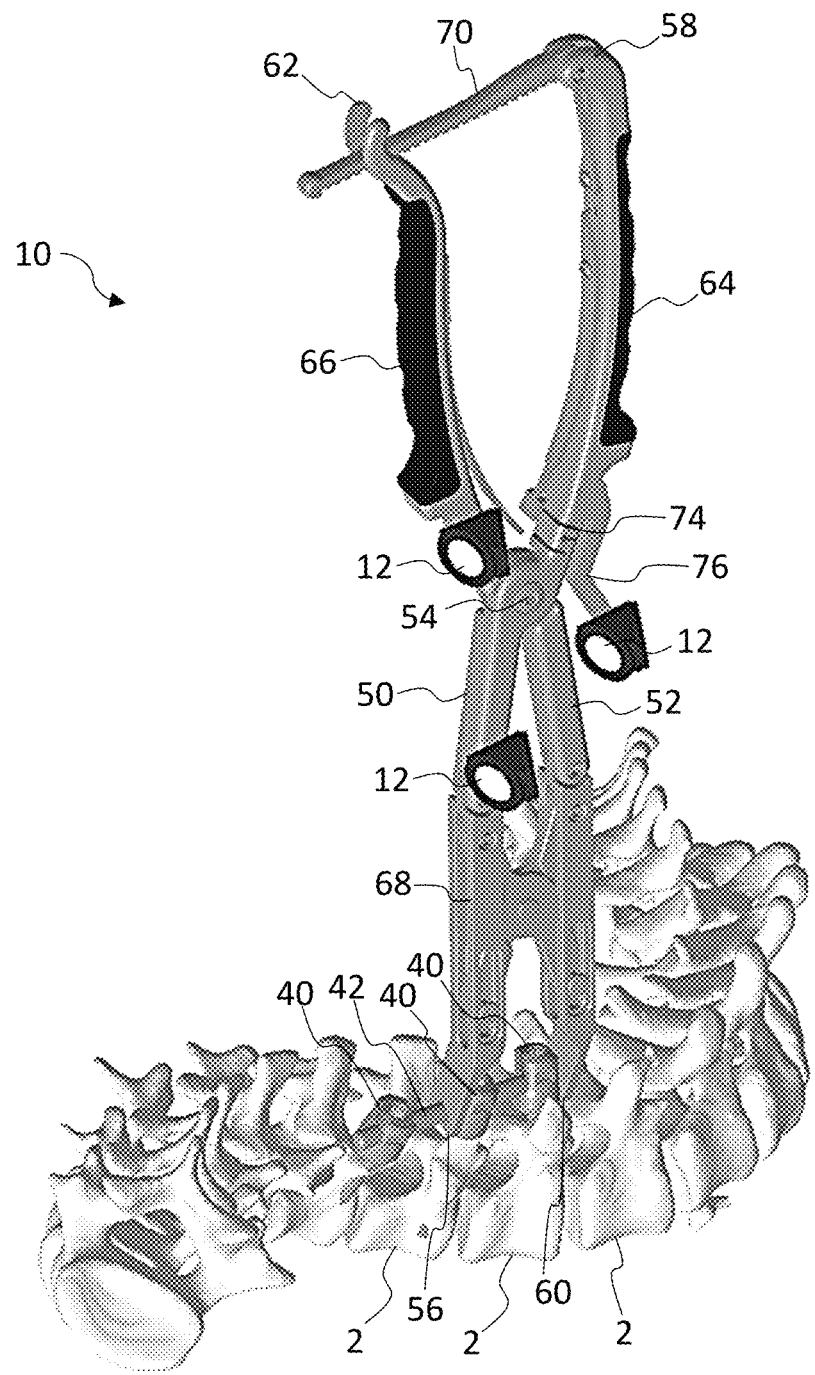
FIG. 1 illustrates a navigated force sensing compressor instrument for repositioning vertebrae according to one embodiment.

Turning now to the drawing, where like numerals indicate like elements throughout, FIG. 1 illustrates a navigated force sensing instrument 10 according to one embodiment. The force sensing instrument 10 may employ optical tracking methods to measure the deflections of load-bearing portions of the instrument. Knowledge of the stiffnesses of portions of the instrument 10 may be used to calculate the force applied to the instrument 10. The navigation functionality may be used to track the location of the instrument 10 and any implants rigidly attached to the instrument 10. The instrument 10 may further be used to characterize the stiffness of the spine. For example, the force measuring instrument 10 may be used to measure the navigated displacements of the spine resulting from applied forces, thereby characterizing the resulting stiffness.

The navigated instruments 10 may include instruments used for applying forces to correct the spine, for example, in compression, distraction, reduction, and/or derotation. The instrument 10 may include a compressor configured to compress vertebrae, including parallel or angled compression. The instrument 10 may include a distractor configured to distract vertebrae, including parallel or angled distraction. The instrument 10 may include a reducer configured to provide movement to translate and/or derotate the spine. The instrument 10 may include a rib pusher configured to apply force to the ribs. Although certain instruments are exemplified herein, it will be appreciated that the navigated force sensing instrument may include any instrumentation utilized in spinal fusion procedures or other surgical procedures.

The navigated instrument 10 includes one or more markers 12, which are viewable and trackable by a navigation and/or robotic platform 20. Infrared signal based position recognition systems may use passive and/or active sensors or markers 12 for tracking the objects. In passive sensors or markers, objects to be tracked may include passive sensors, such as reflective spherical balls or discs, which are positioned at strategic locations on the object to be tracked. Infrared transmitters transmit a signal, and the reflective marker 12 reflect the signal to aid in determining the position of the object in 3D. In active sensors or markers, the objects to be tracked include active infrared transmitters, such as light emitting diodes (LEDs), and generate their own infrared signals for 3D detection.

In one embodiment, the trackable markers 12 may include radiopaque or optical markers. The markers 12 may be suitably shaped, including spherical, spheroid, disc, cylindrical, cube, cuboid, or the like. In one embodiment, the markers 12 coupled to the surgical instrument 10 comprise passive reflective discs for navigation tracking. The discs may be provided in pairs at each marker location. The trackable markers 12 may be coupled to the surgical instrument 10 in any appropriate manner. The trackable markers 12 may include fixed or movable markers used to measure forces to or on the instrument 10 or due to forces of or applied to the associated anatomy. Alternatively, machine vision may be employed to track the instruments 10 without any markers.

Figure 2:
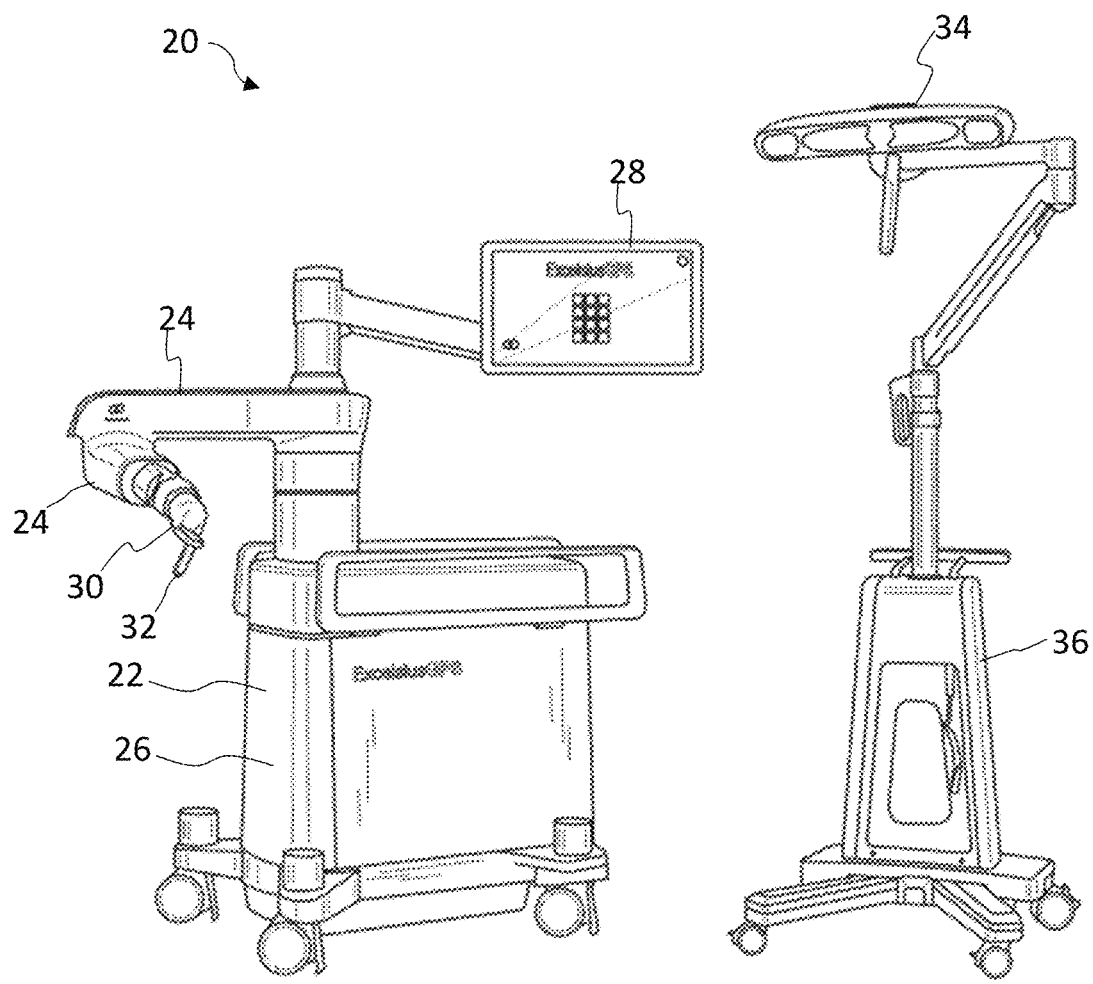
FIG. 2 illustrates an example of a surgical robotic and navigation system.

FIG. 2 illustrates one example of a surgical robotic and navigation system 20. The surgical robot system 20 may include, for example, a surgical robot 22, one or more robot arms 24, a base 26 with one or more computers having a processor, programming, and memory, a display or monitor 28 (or optional wireless tablet) electronically coupled to the computer, and an end-effector 30 including a guide tube 32 electronically coupled to the computer and movable based on commands processed by the computer. The surgical robot system 20 may also utilize a camera 34, for example, positioned on a camera stand 36. The camera stand 36 can have any suitable configuration to move, orient, and support the camera 34 in a desired position. The camera 34 may include any suitable camera or cameras, such as one or more infrared cameras (e.g., bifocal or stereophotogrammetric cameras), able to identify, for example, active and passive tracking markers 12 in a given measurement volume viewable from the perspective of the camera 34. The camera 34 may scan the given measurement volume and detect the light that comes from the markers 12 in order to identify and determine the position of the markers 12 in three-dimensions. For example, passive markers 12 may include retro-reflective markers that reflect infrared light (e.g., they reflect incoming IR radiation into the direction of the incoming light), for example, emitted by illuminators on the camera 34 or another suitable device.

The robotic system 32 may include one or more computer controlled robotic arms 34 to assist surgeons in planning the position of stereotaxic instruments relative to intraoperative patient images. The system 20 includes 2D & 3D imaging software that allows for preoperative planning, navigation, and guidance through a dynamic reference base, navigated instruments and positioning camera for the placement of spine, orthopedic, or other devices. Further examples of surgical robotic and/or navigation systems can be found, for example, in U.S. Pat. Nos. 10,675,094 and 9,782,229, which are incorporated by reference herein in their entireties for all purposes.

With further emphasis on FIG. 1, the force sensing instrument 10 may be a compressor or distractor configured to move vertebrae 2 of the spine, for example, to correct a spinal deformity. FIG. 1 depicts anatomy of the spine and one example of a spinal construct including a plurality of pedicle screws 40 and a spinal rod 42 connected therebetween. The spinal construct may be a temporary construct used to correct the deformity before a permanent construct is installed. Examples of bone fasteners and other implants and rod constructs are described in more detail, for example, in U.S. Pat. No. 10,368,917, which is incorporated by reference herein in its entirety for all purposes. The instrument 10 may be placed onto the spinal rod 42 and/or adjacent to the tulip heads 46 of the screws 40 to make adjustments to the spine.

In one embodiment, the instrument 10 may be a parallel compressor having a first pivoting arm 50 and an opposed second pivoting arm 52 configured to engage the spinal rod 44. The first and second pivoting arms 50, 52 may be interconnected at a center pivot pin 54. In the compressor, the arms 50, 52 may crisscross in a scissor-like fashion at center pivot pin 54. The first pivoting arm 50 extends from distal end 56 to proximal end 58. Similarly, the second pivoting arm 52 extends from distal end 60 to proximal end 62. The distal ends 56, 60 may define recesses or U-shaped free ends sized and configured to receive the spinal rod 44. The proximal ends 58, 62 are manipulable by a user, such as a surgeon. For example, the first and second pivoting arms 50, 52 may each define a handle 64, 66 toward the proximal ends 58, 62, which are configured to be gripped and squeezed by the user. The inner facing portions of the handles 64, 66 may include curved leaf springs configured to apply an opposing force to the handles 64, 66 when squeezed. The parallel compressor 10 may have a slot and pin assembly 68 with interconnected bars that slide along slots via pins, when the handles 64, 66 are manipulated. Examples of a parallel compressor assembly are described in U.S. Pat. No. 6,716,218, which is incorporated by reference herein in its entirety for all purposes. This allows for parallel movement at ends 56, 60 of the instrument 10 such that when opened and closed, the distal ends 56, 60 of the instrument 10 remain parallel to one another.

The instrument 10 may include a ratchet 70 positionable between the proximal ends 58, 62 of the pivoting arms 50, 52 to hold force applied to the screws 40. The ratchet 70 may include a linear body or rail with a plurality teeth defined along the interior of the ratchet 70. A first end of the ratchet 70 may be coupled to one of the pivot arms 58, 62 via a pivot pin and the opposite end of the ratchet 70 may be positionable through a slot in the end of the opposite pivot arm 50, 52. As the ratchet 70 moves through the slot, a pawl therein engages the teeth of the ratchet 70 to thereby incrementally maintain the position of the ends 56, 60 of the arms 50, 52 and the amount of force applied to the vertebrae 2.

Figures 3A, 3B:
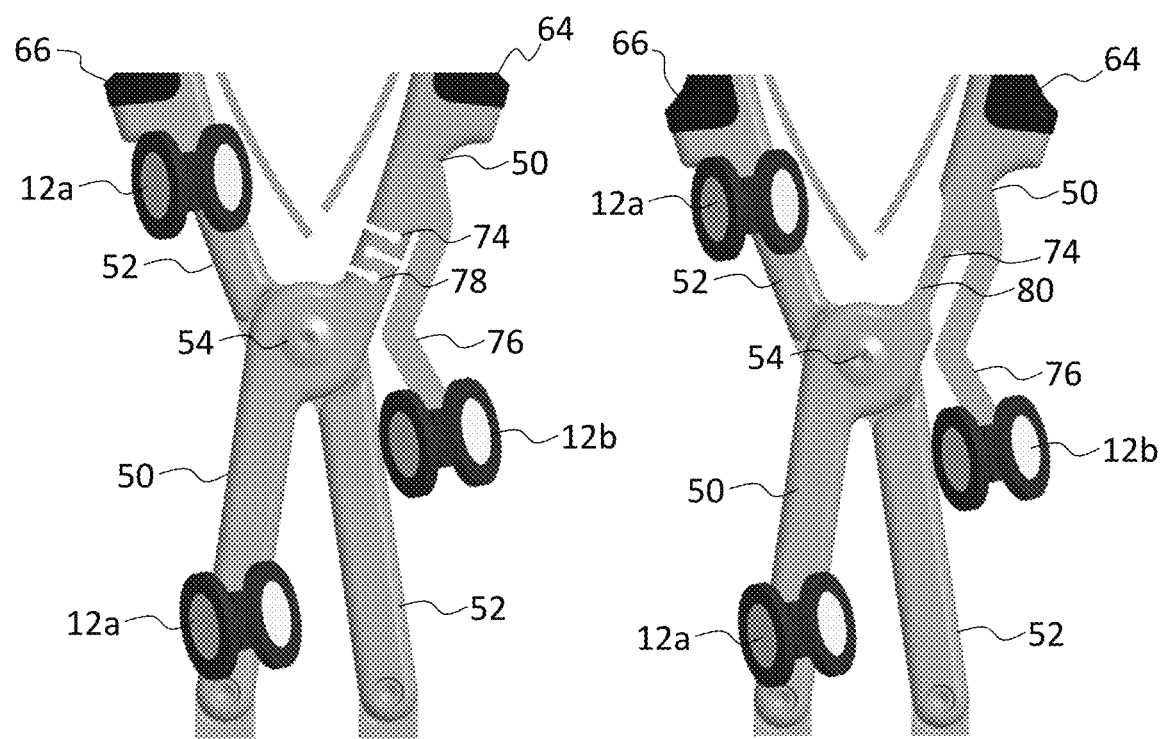
FIGS. 3A-3B show examples of a navigated parallel compressor with a flexible portion having relief cuts and a decreased width, respectively, to measure applied forces.

With further emphasis on FIGS. 3A-3B, the compressor 10 has a flexible portion 74 in one of the handles 64, 66 with a known stiffness. First and second markers 12*a* are affixed on rigid segments of each arm 50, 52. Each marker 12 may be a pair of passive reflective discs. For example, a first rigid marker 12*a* may be attached to the first arm 50 at an arm segment below the center pin 54 and a second rigid marker 12*a* may be attached to the second arm 52 at an arm segment above the center pin 54 on one side of the instrument 10. The relative displacement of these rigid markers 12*a* allows for the tracking of the displacement of the compressor 10. An additional marker 12*b* is attached to the handle portion 64 on the opposite side of the flexible portion 74 from the rigid segment. For example, the movable marker 12*b* may be attached to arm 50, below handle 64, with a lever arm 76. The lever arm 76 may extend distally and the lever arm 76 may be bent to follow the contour of the arms 50, 52. The marker 12*b*, for example, including a pair of passive reflective discs, may be attached to the free end of the lever arm 76. The relative motion of the additional marker 12*b* relative to the markers 12*a* on the rigid segments results from the stiffness of the flexible portion 74 and is measurable by the navigation system 20.

The flexible portion 74 may be located in an upper portion or arm segment of one of the arms 50, 52 between the handle 64, 66 and the pivot pin 54. The flexible portion 74 has the ability to deform under load or force. The flexible portion 74 has a known stiffness or amount of force which needs to be applied to achieve deformation (e.g., force per unit distance). The flexible portion 74 may be formed of one or more relief cuts 78 including linear or helical cuts, reduced segments 80 having a reduced width, depth, or diameter, flexible material sections, or other flexures or areas configured to impart flexibility having a known stiffness to a portion of the instrument 10. In the embodiment shown in FIG. 3A, the flexible portion 74 may be located in an upper segment of arm 50 and may include one or multiple relief cuts 78. The relief cuts 78 may include a series of alternating cuts on opposite sides of the arm 50. The relief cuts 78 may include a plurality of linear cuts arranged in parallel. For example, a first cut 78 may extend into arm 50 from an inner portion of arm 50, a second cut 78 positioned below the first cut 78 may extend into arm 50 from an outer portion of arm 50, and a third cut 78 positioned below the second cut 78 may extend into the arm 50 from the inner portion of the arm 50. It will be appreciated that the number, type, and/or orientation of cuts may be selected to achieve the desired flexibility and stiffness.

In the embodiment shown in FIG. 3B, the relief cuts 78 are replaced with a segment 80 having a decreased width, depth, or diameter. The reduced segment 80 may be narrowed along arm 50 between the pivot pin 54 and the attachment of lever arm 76 to impart a given flexibility or stiffness to the additional marker 12*b*. In an alternative embodiment, the flexible portion 74 may be made of a flexible material, such as Nitinol, titanium, or a plastic such as polyetheretherketone (PEEK). The flexible portion 74 and lever arm 76 of the additional marker 12*b* are configured such that its stiffness results in appropriate resolution for force measurements. For example, if the desired force resolution is 10N and the accuracy of the tracking system 20 is 0.2 mm, the stiffness of the flexible portion 74 and lever arm 76 results in at least 50 N/mm of stiffness. It will be appreciated that any suitable stiffness or flexibility may be used to calculate the resulting force measurements.

Figure 4A:
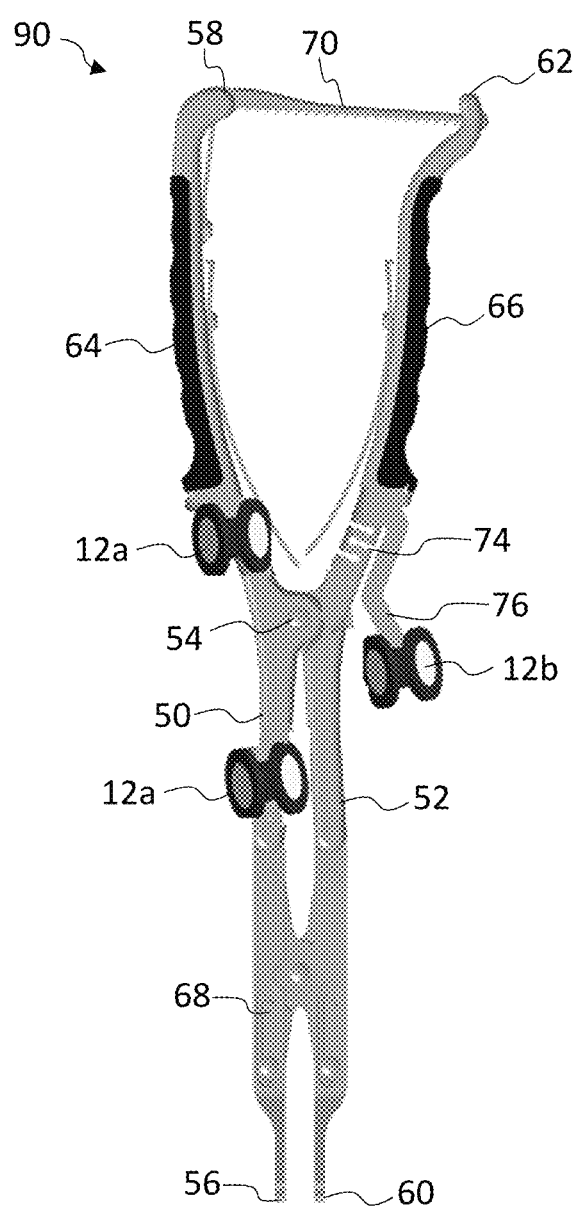
FIGS. 4A-4B shows examples of a parallel distractor and a simple compressor, respectively, that may include a flexible portion to measure applied forces.
Figure 4B:
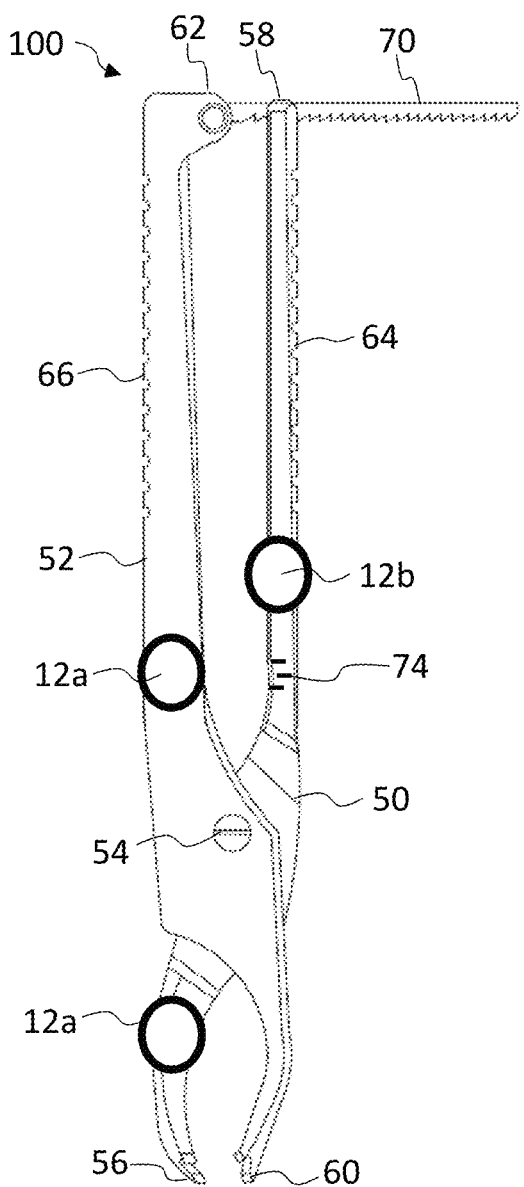

Turning now to FIGS. 4A-4B, the parallel compressor 10 may be replaced with another type of instrument, with the same type of functionality of flexible portion 74 and markers 12*a*, 12*b* to measure applied force. FIG. 4A shows an example of a parallel distractor 90 with varied pivot points that result in distracting motion. Parallel distractor 90 is similar to parallel compressor 10 except the arms 50, 52 are modified to be complimentary such that the distal ends 56, 60 are configured to move away from one another to distract the vertebrae 2. Similar to compressor 10, distractor 90 includes flexible portion 74 with a known stiffness. First and second markers 12*a* are affixed on rigid segments of arm 50. For example, a first rigid marker 12*a* may be attached to the first arm 50 at an arm segment below the center pin 54 and a second rigid marker 12*a* may be attached to the first arm 50 at an arm segment above the center pin 54 on one side of the instrument 10. The relative displacement of these rigid markers 12*a* allows for the tracking of the displacement of the distractor 90. An additional marker 12*b* is attached to the handle portion 66 on the opposite side of the flexible portion 74 from the rigid segment. For example, the movable marker 12*b* may be attached to second arm 52, below handle 66, to a free end of the lever arm 76. The relative motion of the additional marker 12*b* relative to the markers 12*a* on the rigid segments results from the stiffness of the flexible portion 74 and is measurable by the navigation system 20.

The flexible portion 74 and tracking markers 12 may also be employed in simple compressors and distractors with a single pivot point instead of parallel linkages. FIG. 4B provides an example of a simple compressor 100, with the same type of functionality of flexible portion 74 and markers 12*a*, 12*b* to measure force. The compressor 100 includes a flexible portion 74 in one of the handles 64, 66 with a known stiffness. First and second markers 12*a* are affixed on rigid segments of each arm 50, 52. The relative displacement of these rigid markers 12*a* allows for the tracking of the displacement of the compressor 10. An additional marker 12*b* is attached to the handle portion 64 on the opposite side of the flexible portion 74 from the rigid segment. A lever arm may or may not be provided. The relative motion of the additional marker 12*b* relative to the markers 12*a* on the rigid segments results from the stiffness of the flexible portion 74, which is measurable by the navigation system 20. These variations may allow for parallel or angled compression or distraction. It will be appreciated that the location, number, and type of tracking markers 12*a*, 12*b*, the location and type of flexible portion(s) 74, and the instrument type may be varied to achieve the desired functionality, tracking, and resulting measurement of forces on the instrument and/or the spine.

Figure 5A:
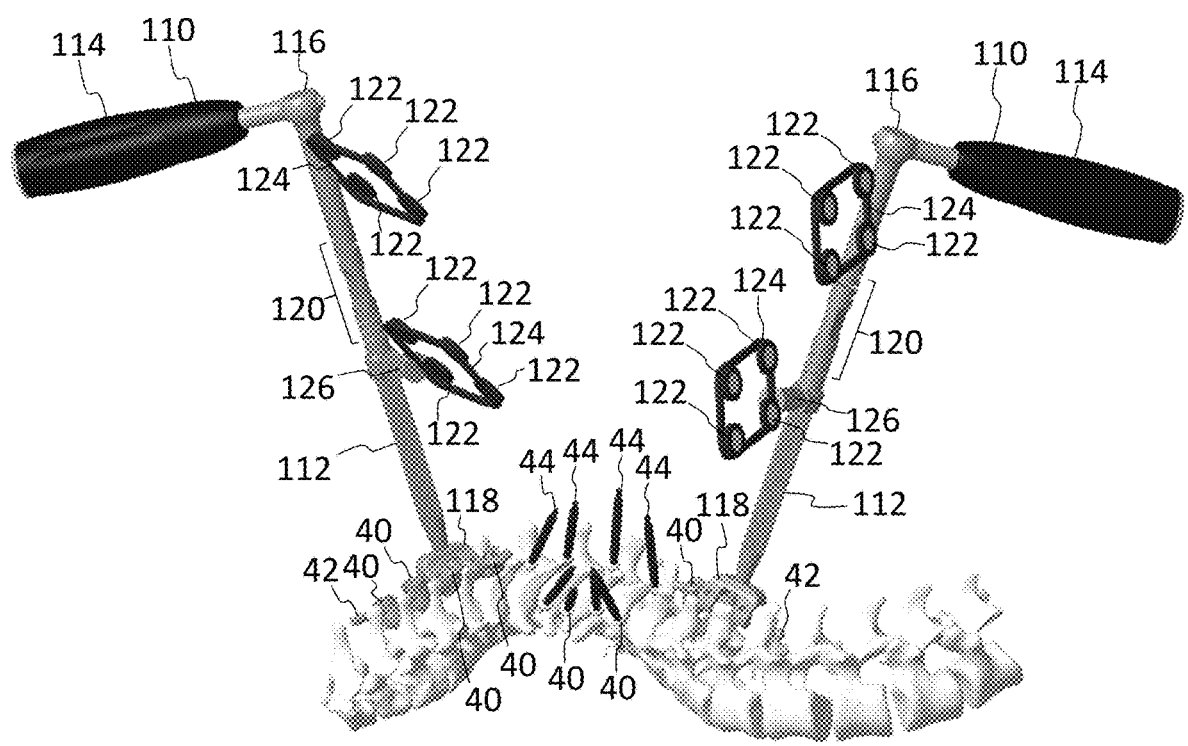
FIGS. 5A-5C illustrate navigated rod link reducers with a flexible portion to correct a spinal curvature according to one embodiment.
Figure 5B:
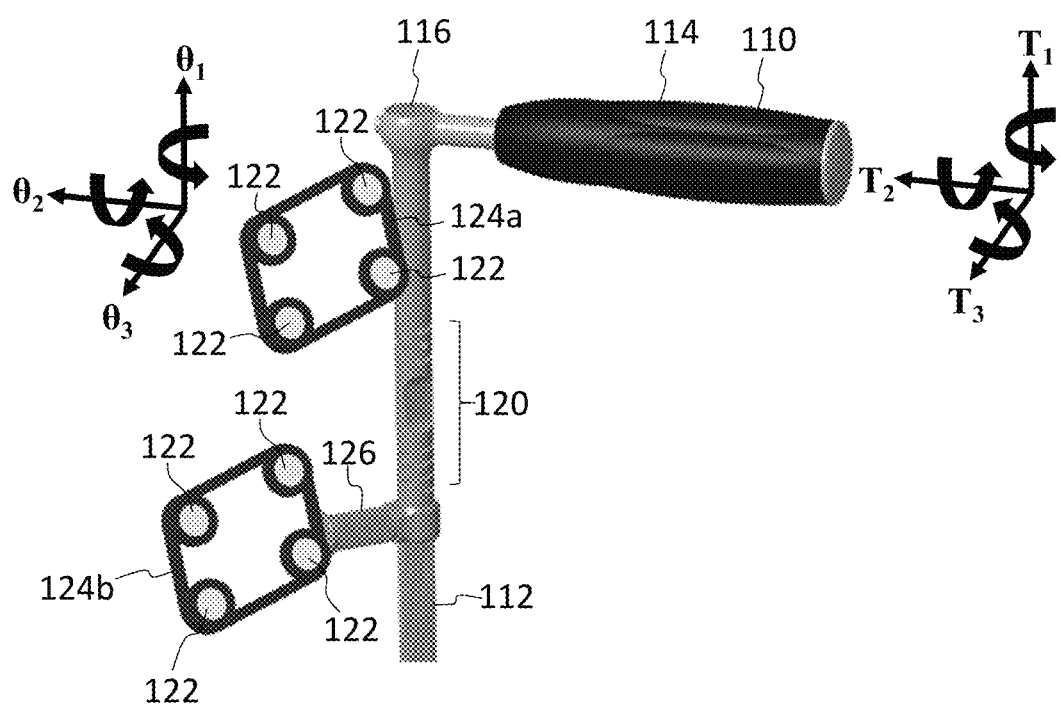
Figure 5C:
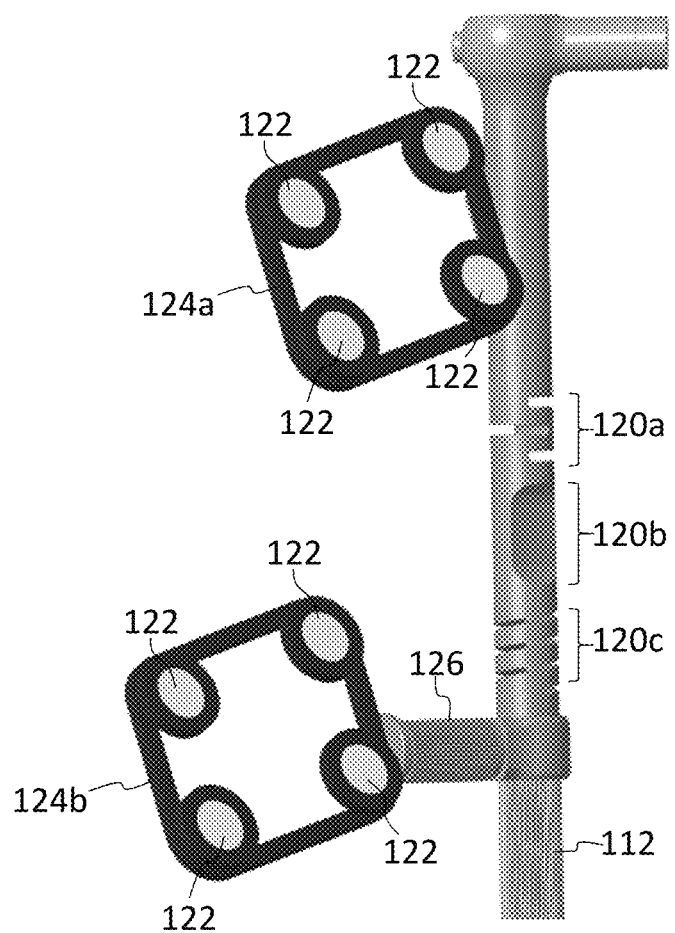

Turning now to FIGS. 5A-5C, a rod link reducer instrument 110 is shown according to one embodiment. FIG. 5A depicts anatomy of the spine and two temporary spinal constructs each including a spinal rod 42 attached to pedicle screws 40, a pair of rod link reducers 110 manipulating the respective spinal constructs, and a plurality of screw extenders 44 attached to pedicle screws 40 for monitoring the positioning of the spine via the robotic and/or navigation system 20. Examples of rod link reducers and methods for correcting spinal deformities are described in more detail, for example, in U.S. Pat. Nos. 10,869,699 and 10,736,671, which are incorporated by reference herein in their entireties for all purposes.

The rod link reducer 110 includes a manipulating arm or manipulator rod 112 and a handle 114. The manipulator rod 112 has a first end 116, a second end 118, and an elongate body extending along a body axis between first end 116 and second end 118. The handle 114 may be removably attachable to the first end 116 of the manipulator rod 112. The handle 114 may be positioned generally orthogonal to the body axis of the manipulator rod 112. The handle 114 is adapted to maneuver the manipulator rod 112 as desired by the surgeon. The second end 118 of manipulator rod 112 includes a distal tip with a receiver adapted to releasably secure the temporary spinal rod construct therein. The spinal rod 42 may be retained within the distal receiver of the rod link reducer 110 via one or more securing members, such as set screws, configured to engage and secure the spinal rod 42. It will be appreciated that the manipulator rod 112 may be temporarily secured to the temporary spinal construct in any suitable manner and manipulated to perform the desired surgical corrections.

Similar to instrument 10, the rod link reducer 110 has one or more flexible portions 120 and markers 122 for navigation tracking configured to determine the forces applied to the instrument 110 and/or of the spine. The flexible portion(s) 120 may be provided along the length of the manipulator rod 112. With further emphasis on FIG. 5C, the flexible portion 120 may include one or more flexures, such as one or more linear relief cuts 120a, decreased widths or diameters 120b, helical relief cuts 120c, flexible materials such as Nitinol, titanium, or a plastic such as PEEK, or other features to impart a given flexibility or stiffness to the manipulator rod 112. In the embodiment shown, the flexible portion 120 of the manipulator rod 112 includes linear relief cuts 120a positioned proximally, helical relief cuts 120c positioned distally, and a reduced diameter section 120b positioned between the linear and helical cuts 120a, 120c. It will be appreciated that the number, type, and location of flexible portion(s) 120 may be selected to achieve the desired flexibility and stiffness.

The rod link reducer 110 includes a plurality of tracking markers 122, such as passive reflective discs. The tracking markers 122 may be arranged in an array 124. The array 124 may include a group of markers 122, for example, four markers 122 arranged in a given order or pattern. As shown, the array 124 of markers 122 may form a diamond or square pattern, for example. The array 124 may be attached directly to the manipulator rod 112 or may be affixed with a connector bar 126. With further emphasis on FIG. 5C, each rod link reducer 110 may include a proximal array 124a located proximally and a distal array 124b located distally along manipulator arm 112. In one embodiment, the rod link reducer 110 has flexible portion 120 separating the distal array 124b from the proximal array 124a. The distal array 124b is rigidly attached to the lower portion of the manipulating arm 112 with connector bar 126. An outer surface of the manipulating arm 112 may be knurled, for example, with a straight line pattern or diamond pattern, to enhance connection. The distal array 124 may be movable to a desired location along the length of the manipulating arm 112 below flexible portion 120. The relative motion of the proximal array 124a with respect to the fixed distal array 124b allows the recreation of applied torques to the proximal handle 114.

As shown in FIG. 5A, screw extenders 44 may be attached to the bone screws 44 to provide for additional tracking of the spine by the navigation system 20. For example, the screw extenders 44 may have additional markers configured to be tracked by the navigation system 20. The screw extenders 44, attached to levels not rigidly attached to the rod link reducer(s) 110, enable the tracking of these levels in addition to levels tracked by the rod link reducer(s) 110.

With further emphasis on FIG. 5B, the 3D tracking of the arrays 124 enables the measurement of three angles ($\theta_1$, $\theta_2$, $\theta_3$) from the array 124a which correspond to three applied torque ($T_1$, $T_2$, $T_3$) directions through the known stiffness of the flexible portion 120. The flexures 120 may be designed and oriented to give varying stiffnesses in each of the three torque directions to allow measurement of the applied torques at varying resolutions and magnitudes based on the amount of torque applied in each direction. For example, in the embodiment shown, the linear relief cuts 120a, decreased width, 120b, and helical cuts 120c result in decreased stiffnesses in different directions due to the varying orientation of removed material. In this manner, the rod link reducer 110 enables the measurement of the spine's stiffness as surgeons are achieving correction and may be directly utilized to design the spinal rod contour.

Figure 6A:
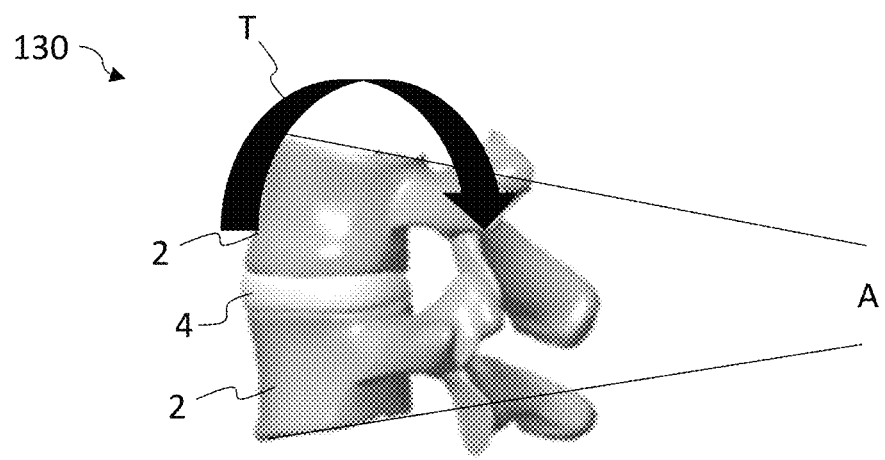
FIGS. 6A-6B show single motion and two motion segments, respectively, and the application of torques and changes in angle characterizing the stiffness of the spine in multiple directions.
Figure 6B:
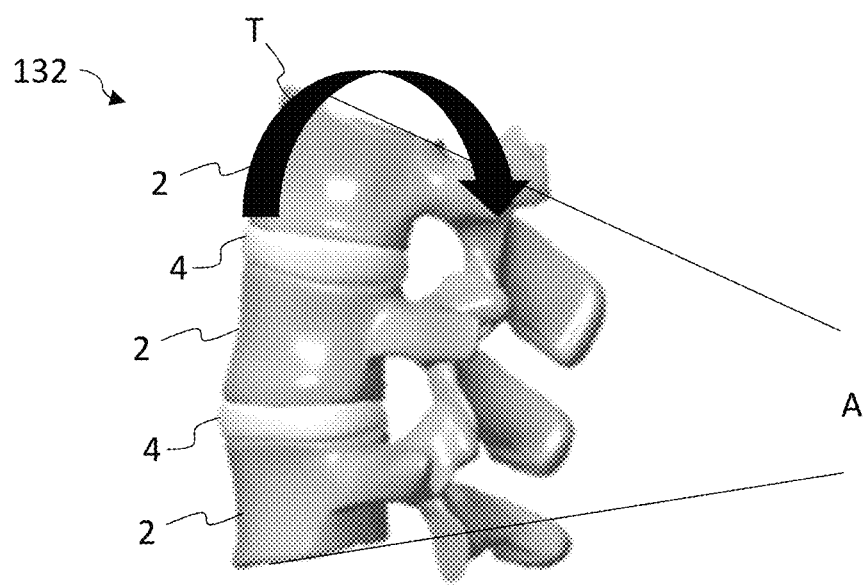
Figure 7:
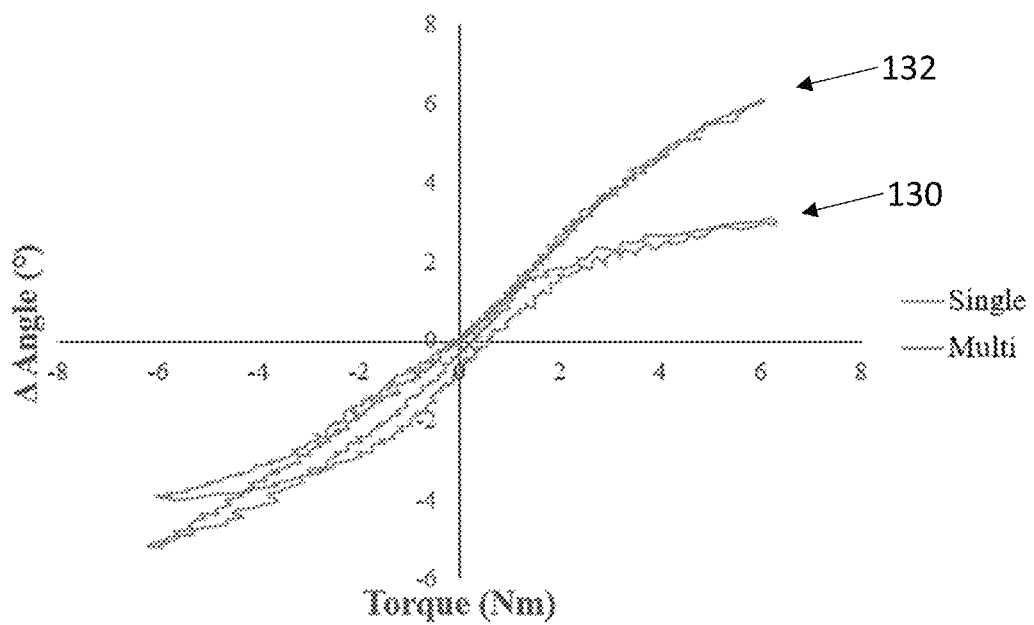
FIG. 7 is a graph recording measured torques and change in angle trace of the single motion and two motion segments.

Turning now to FIGS. 6A-6B and 7, the force sensing instruments 10, 110 may be used in conjunction with navigated screw extenders 44 to measure applied forces, locations of applied forces, and resulting displacements to characterize the stiffness of the spine. FIG. 6A shows a single motion segment 130 of the spine including two adjacent vertebrae 2 and the intervertebral disc 4 between them. FIG. 6B shows a multi-motion or two motion segment 132 including three adjacent vertebrae 2 and intervertebral discs 4. During the deformity procedure, torques T may be applied to the motion segments 130, 132 and the angle A of the motion segments 130, 132 may change.

FIG. 7 depicts a graph of a torque to change in angle trace of the single motion segment 130 and two motion segments 132 in flexion-extension. Recording measured torques T and resulting changes in angles A of the vertebrae 2 allows the measurement of the spine's nonlinear stiffness across one or multiple levels. Application of forces/torques and measurements of displacements/angle changes in multiple directions (lateral bending, axial rotation, etc.) allows the characterization of the stiffness of the spine in multiple directions.

The navigated rod link reducer 110 allows for the measurement of applied torques ($T_1$, $T_2$, $T_3$) in each direction and the resulting displacements of attached implants and intermediate levels. These measured torques and changes in angles may be used to characterize the stiffness of multiple segments 132 or single segments 130. Additional instruments may be used to characterize the stiffness of the spine in varying directions and orientations.

Figure 8A:
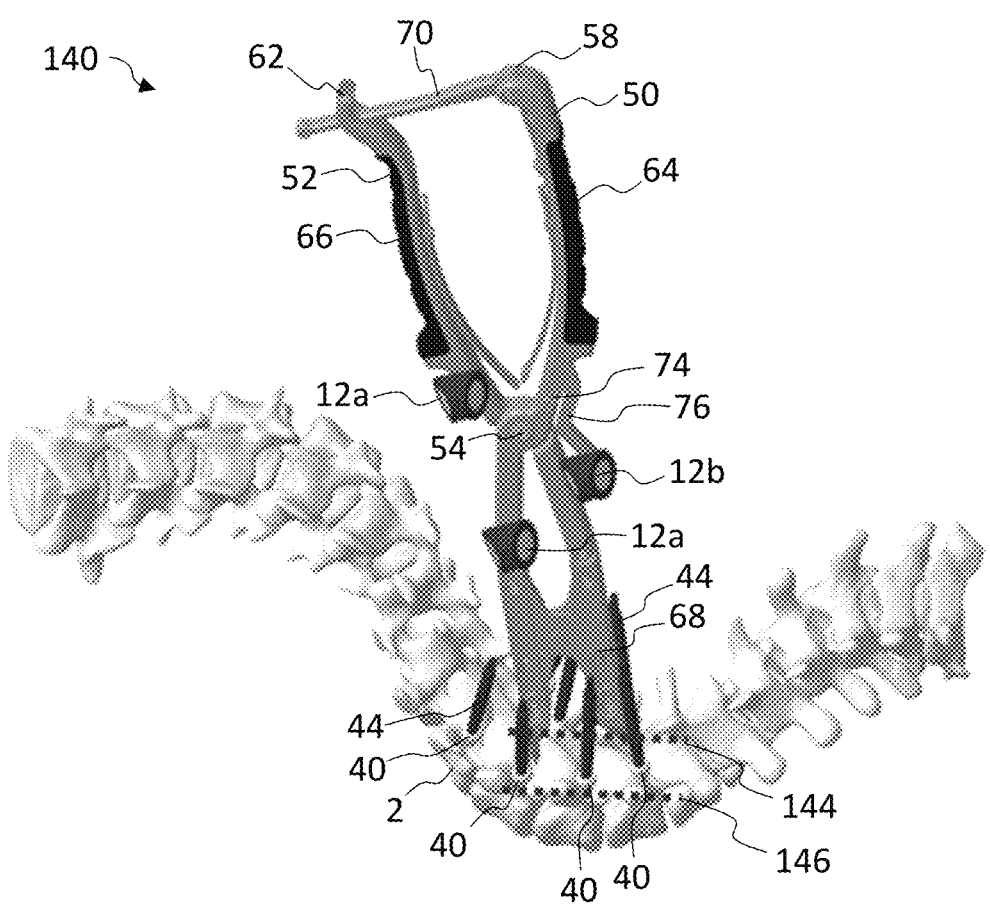
FIGS. 8A-8B shows a navigated lamina compressor for applying forces to the spine and a close-up of the view of the lamina compressor tip according to one embodiment.
Figure 8B:
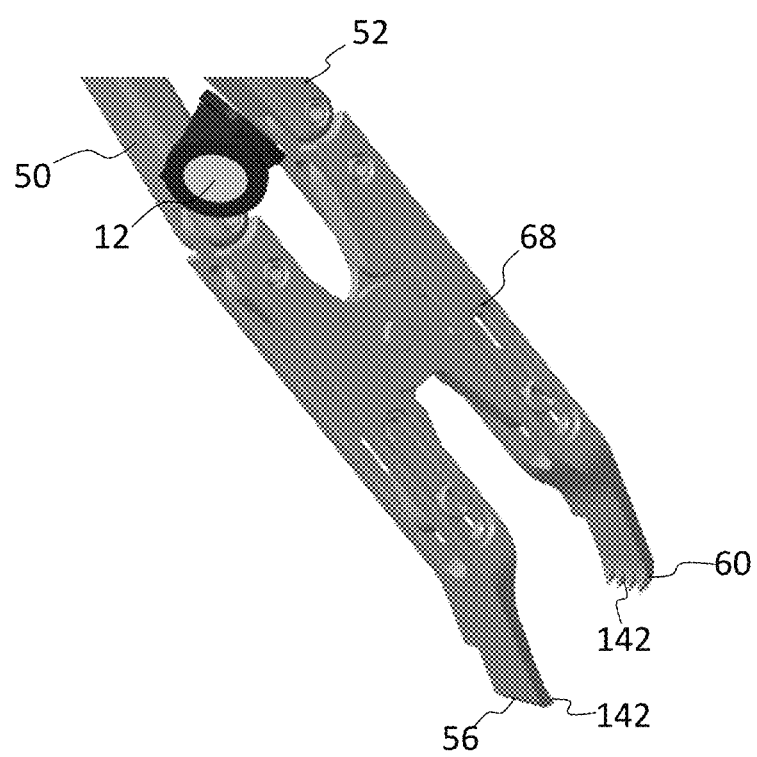

Turning now to FIGS. 8A-8B, a navigated force sensing compressor or distractor 140 is shown according to another embodiment. Lamina compressor 140 is the same as parallel compressor 10 except compressor 140 has lamina engaging claws 142 at the distal ends 56, 60. In this case, instead of engaging the rod 42 and screw heads 40, the lamina compressor 140 directly contacts the lamina of the vertebrae 2 to provide a compression or distraction force. As best seen in FIG. 8B, the distal tips 56, 60 of the lamina compressor 140 include claws 142 or lamina engaging features that engage the lamina. The claws 142 may include pointed teeth or rake teeth. For the compressor, the teeth may be curved or angled inward to point toward one another.

The markers 12a on rigid segments allow the tracking of the tips 56, 60 of the instrument 140, and the additional marker 12b allows the measurement of applied compression forces. Screw extenders 44 enable tracking of resulting angles and displacements of the vertebrae 2. The lamina compressor or distractor instrument 140 enables the application and measurement of forces across one or two vertebrae 2 and the monitoring of resulting angles A from the levels manipulated or adjacent levels which also have screw extenders 44. Applications of the forces at the midline 144 of the lamina results in measurement of the spine's sagittal flexion-extension stiffness, while application of forces lateral to midline 146 on the lamina or transverse process allow measurement of the coronal lateral bending stiffness. The lamina compressor or distractor 140 is configured to provide an assessment of the spine's stiffness during the operation. It will be appreciated that the lamina instrument may be embodied as a compressor or distractor with either multiple linkages for parallel actuation, or a simple single pivot point for angled actuation.

Figure 9A:
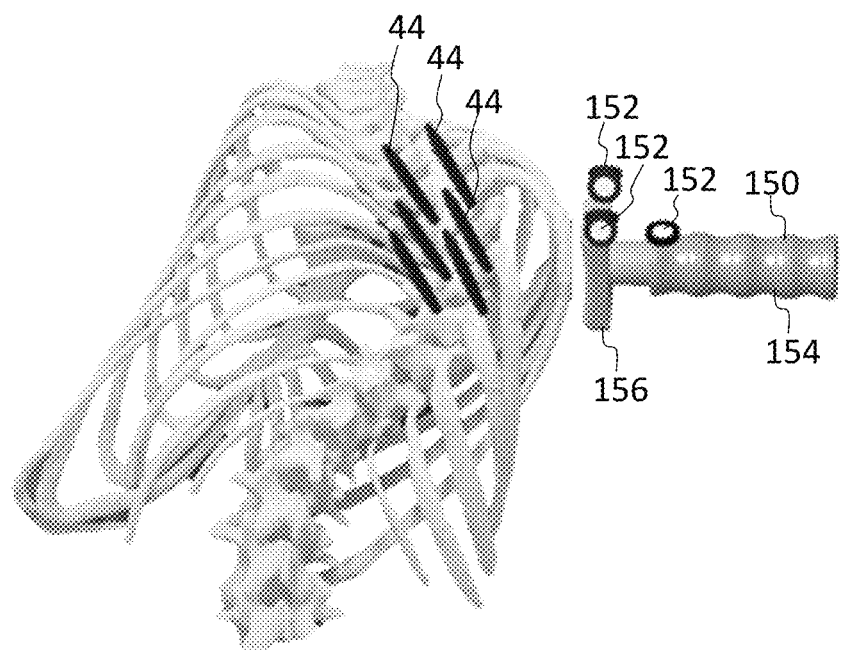
FIGS. 9A-9B show a navigated force sensing rib pusher for applying force on ribs and a cross-section of the rib pusher according to one embodiment.
Figure 9B:
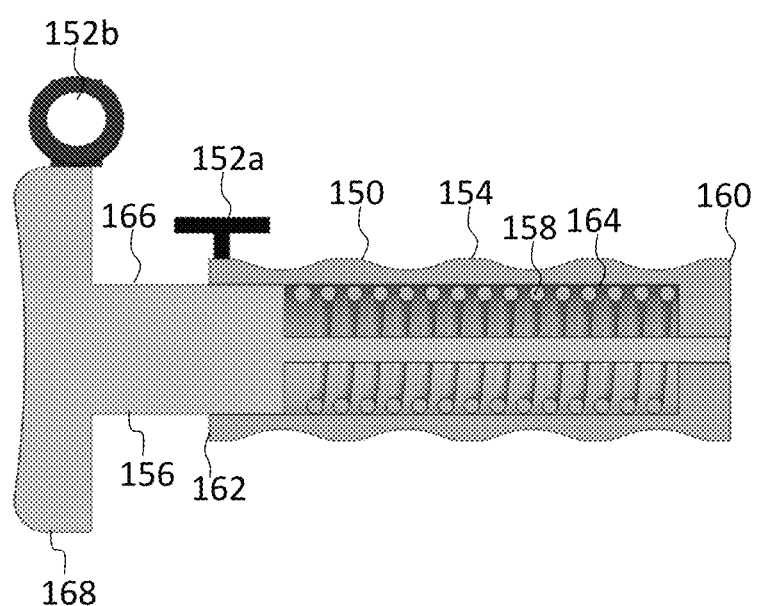

Turning now to FIGS. 9A-9B, a navigated force sensing rib pusher 150 is shown according to one embodiment. FIG. 9A shows anatomy of the ribs and spine, the navigated force sensing rib pusher 150, and a plurality of screw extenders 44 attached to bone screws 40. The navigated force sensing rib pusher 150 is used to apply a force on ribs and the location of the applied force is navigated. Screw extenders 44 monitor the resulting displacements in vertebrae 2. The rib pusher 150 includes a plurality of markers 152, such as passive reflective discs, configured to be tracked by the navigation system 20.

As best seen in FIG. 9B, the navigated force sensing rib pusher 150 includes a body handle 154, a plunger 156, and a spring 158. The handle 154 extends from a proximal end 160 to a distal end 162 along a longitudinal axis. The exterior of the handle 154 defines a grip configured to be held by the user. The interior of the handle 154 is hollow and defines a cavity 164 for receiving the spring 158 and a portion of the plunger 156. The plunger 156 includes a piston 166 and a flange 168. The piston 166 of the plunger 156 is receivable inside the cavity 164 at the distal end 162 of the handle 154 and is configured to move along the longitudinal axis of the handle 154. The flange 168 is attached to a distal end of the piston 166 and includes an enlarged face configured to contact and apply a force to the ribs of the patient. A fixed marker 152a is affixed on the end 162 of the handle 154. Two pairs of disc markers 152b, movable when the plunger 156 moves, are affixed onto the flange 168 of the plunger 156. Displacement of the body handle 154 with respect to the plunger 156 is navigated through the markers 152 on both components and multiplied by the stiffness of the spring 158 to calculate the applied force. The markers 152b on the plunger 156 enable navigation of the location of applied forces. The rib pusher 150 enables assessment of the spine's stiffness as the surgeons are performing releases and provides feedback on if the spine has been sufficiently released to achieve subsequent corrections.

Figure 10A:
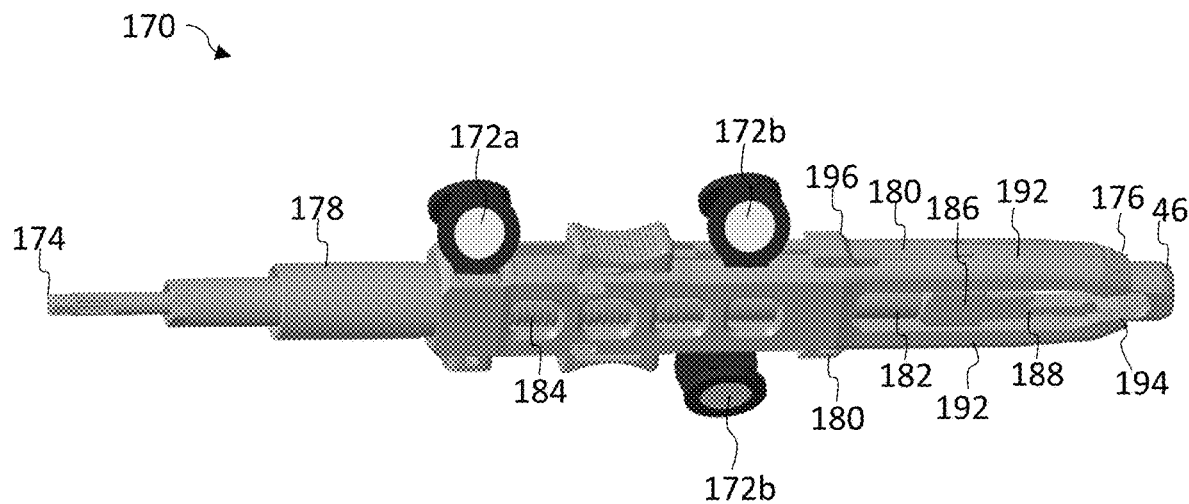
FIGS. 10A-10B show a navigated force sensing reducer for applying reduction forces to the spinal rod and an engagement tab of the reducer according to one embodiment.
Figure 10B:
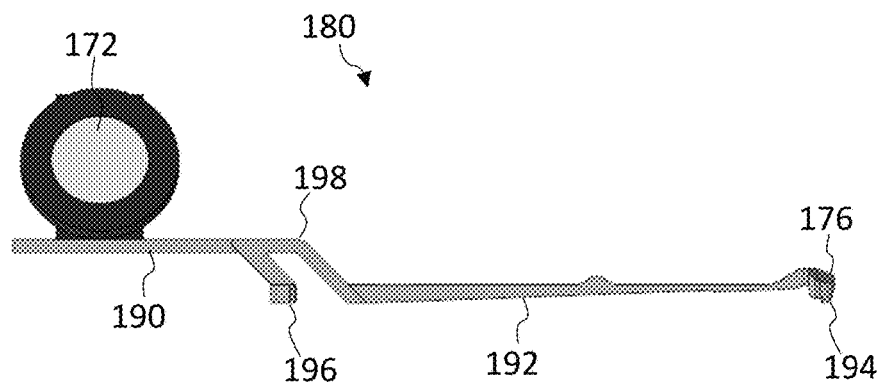

Turning now to FIGS. 10A-10B, a navigated reducer 170 is shown according to one embodiment. The navigated reducer 170 includes a plurality of markers 172, such as passive reflective discs, configured to be tracked by the navigation system 20. The navigated reducer 170 allows for the measurement of corrective forces placed on the spine by the surgeon. The reducer 170 extends from a proximal end 174 to a distal end 176 along a central longitudinal axis. The proximal end 174 may be configured to attach to a handle (not shown). The distal end 176 is configured to surround and grasp a screw head or modular tulip 46 configured to be attached to a modular bone screw 40. Examples of modular tulip assemblies, bone fasteners, and other implants and rod constructs are described in more detail, for example, in U.S. Pat. No. 10,368,917, which is incorporated by reference herein in its entirety for all purposes.

As best seen in FIG. 10A, the reducer 170 includes a body 178, a pair of engagement tabs 180, and a central pusher 182. The body 178 of the reducer 178 defines a hollow tube. The pusher 182 threads through the body 178 to apply reduction forces to the spinal rod 42. The pusher 182 may include a rod 184 and a block 186 aligned along the central longitudinal axis. The rod 184 may be threaded along a proximal portion to threadedly engage the body 178. The block 186 may have a recessed distal end 188 configured to contact and apply force to the spinal rod 42. The screw head or modular tulip 46 is rigidly attached to the body 178 by the engagement tabs 180.

With further emphasis on FIG. 10B, one engagement tab 180 of the reducer 170 is shown in more detail. It will be appreciated that the pair of engagement tabs 180 are identical or mirror images of one another. Each engagement tab 180 has a proximal section 190 and a distal section 192. The distal section 192 may be stepped down or inward relative to the proximal section 190. The distal section 192 terminates at a free end, which acts as the implant engagement portion 194. The implant engagement portion 194 may have inward facing friction enhancing surfaces configured for gripping the outside of the tulip head 46. The engagement tabs 180 are attached to the body 178 at a connecting portion 196 adjacent to a flexure 198, which connects to the implant engagement portion 194. The connecting portion 196 may include a branch member projecting inward from the proximal section 190 of the engagement tab 180. The connecting portion 196 may be angled toward the distal end 176. The flexure 198 may include a bent section, reduced thickness, relief cut, or other features configured to impart flexibility. The flexure 198 may include a bent or sloped section connecting the distal section 192 to the proximal section 190, which amplifies any movement of the distal section 192.

A first marker 172a, including a pair of passive reflective discs, may be attached to the body 178 of the reducer 170. The first marker 172a may act as a fixed marker. A movable marker 172b, including a pair of passive reflective discs, may be attached to each of the engagement tabs 180. In this manner, the movable markers 172b move with the engagement tabs 180 and reflect the amount of force applied to the engagement tabs 180. Tension applied to the engagement tabs 180 during reduction and derotation causes the flexure 198 to move and rotate the movable markers 172b. The proximal section 190 acts as an extended moment arm, and extends off of the flexure 198 to magnify the displacement of the movable markers 172b. Reduction loads purely in tension may result in equal motion of left and right movable markers 172b. Derotation loads may result in differential motion of the left and right movable markers 172b. The combination of these motions result in the simultaneous measurement of both reduction and derotation loads.

Figure 11A:
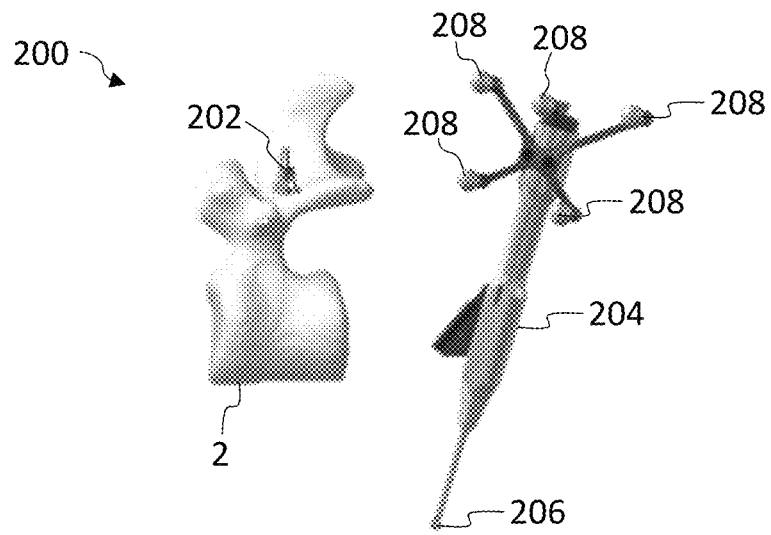
FIGS. 11A-11B show registration methods including one with bone fiducials attached to vertebrae having their locations registered using a registration wand and another method with a wand to trace the posterior elements of vertebrae to register the surface of the vertebrae to the scan, respectively.
Figure 11B:
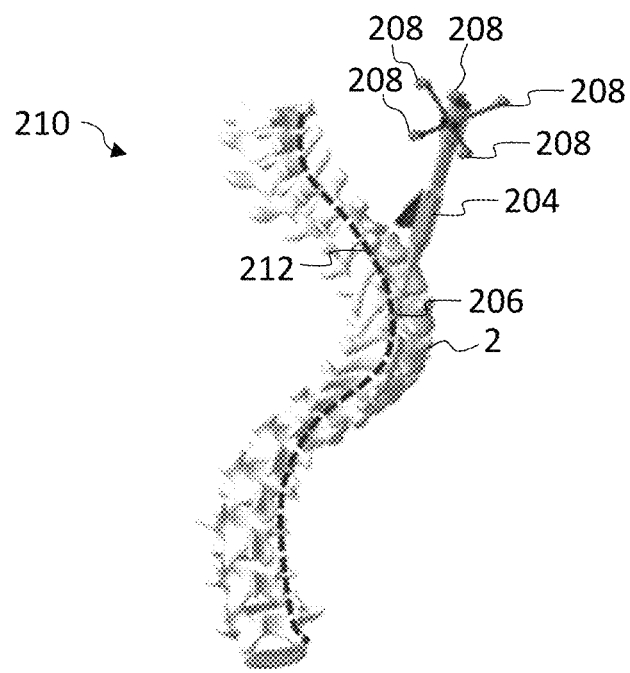

Turning now to FIGS. 11A-11B, alternative registration systems and methods to characterize the stiffness of the spine are shown. FIG. 11A exemplifies a bone fiducial registration system 200 and FIG. 11B shows a posterior element tracing system 210. In FIG. 11A, bone fiducials 202 are attached to vertebrae 2 in order to have their locations registered using a registration wand 204. Similar to screw extenders 44, the bone fiducials 202 may be used to navigate the location of vertebrae 2. The registration wand 204 may include a body having a distal tip 206 configured to touch each of the fiducials 202. The registration wand 204 has a plurality of markers 208 configured to be tracked by the navigation system 20. For example, the tracking markers 208 may include an array of passive spherical balls configured to identify and track the wand 204. As the user touches the distal tip 206 to each of the bone fiducials 202, the fiducials 202 have their locations registered and mapped by the navigation system 20.

In FIG. 11B, the registration wand 204 is used to trace the posterior elements of vertebrae 2 to register the surface of the vertebrae 2 to the scan. The user moves the tip 206 of the registration wand 204 along the spine, for example, along dotted line 212, to register and map its location. In these embodiments, the user is able to manually apply forces and record the resulting displacements. This process may be repeated multiple times to achieve the resolution necessary to characterize the stiffness of the spine.

The systems and methods of measuring forces described herein are easily adaptable into instrumentation utilized in spinal fusion procedures using navigation technology, which may be employed in the surgical procedures. No additional electronics are required, which decreases the complexity and cost of these instruments and alleviates potential challenges with sterilization.

The instrument described herein provide the ability to measure applied forces and/or measure the spine's stiffness. Display of these forces to the surgeon may enable them to take action to better distribute corrective forces, avoid over-stressing the bone-screw interface, and assess other effects on patient care, such as the likelihood of subsequent complications, like proximal junctional kyphosis.

These measurements may also be utilized by a system to provide further analysis to characterize the spine's stiffness. The stiffness measurements may be used to optimize the contour of spinal rods used to achieve correction instead of over-contouring the spinal rod to achieve the desired correction. This stiffness may also be relayed to the surgeon to provide feedback if the spine has been sufficiently released to achieve correction without over-stressing the bone-screw interface and provide guidance if additional releases need to be performed.

The instruments provide the ability to measure the spine's stiffness at single motion segments, across regions of the spine, and in varying directions. The instruments enable the measurement of corrective forces placed on the spine in compression, distraction, reduction, and/or derotation. This allows the surgeon to distribute loads across multiple segments and avoid over-stressing the bone-screw interface and causing pullout or plow intraoperatively, or postoperative failure once patient loading additionally stresses the hardware.

Figure 12:
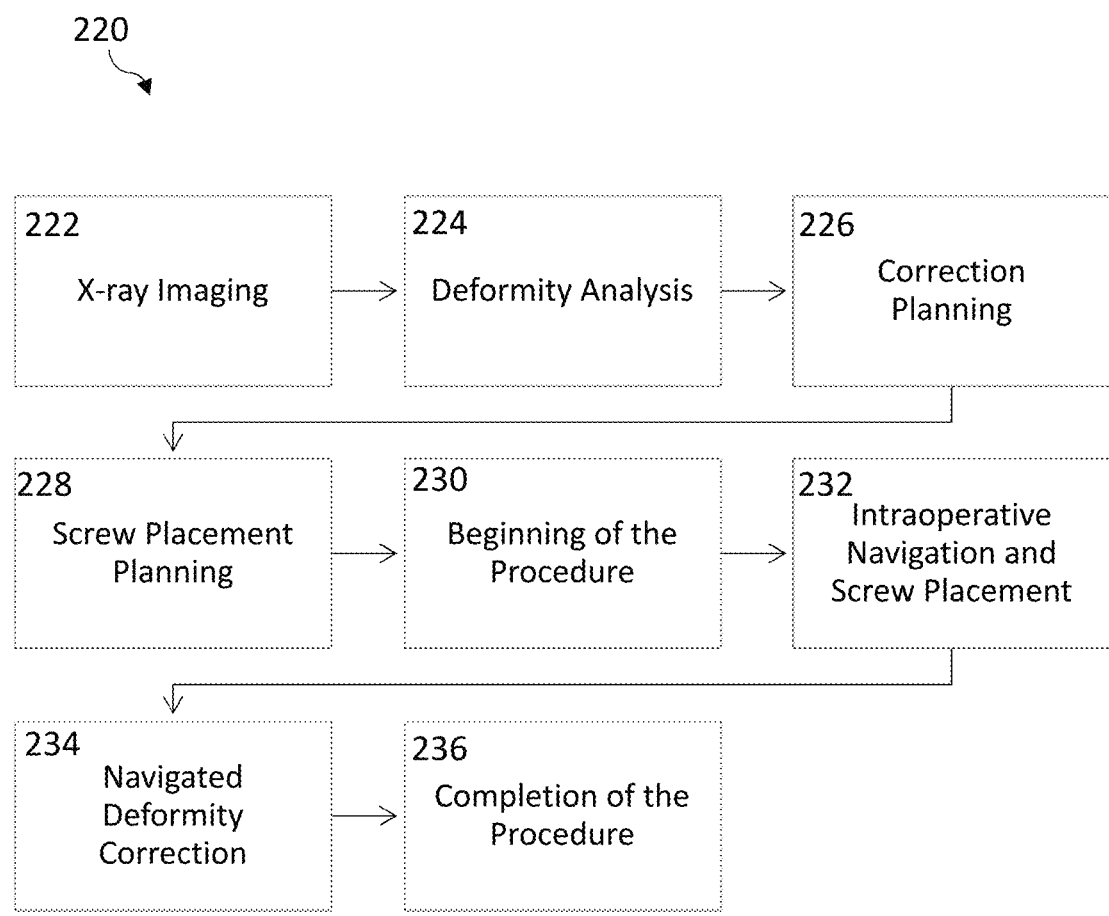
FIG. 12 shows a workflow of the navigated and robotic instruments according to one embodiment.

Turning now to FIG. 12, a workflow 220 of the navigated and robotic instruments is shown according to one embodiment. The workflow 220 may include the following steps: x-ray imaging 222, deformity analysis 224, correction planning 226, screw placement planning 228, beginning the procedure 230, intraoperative navigation and screw placement 232, navigated deformity correction 234, and completion of the procedure 236. The x-ray imaging 222 may include a 3D computerized tomography (CT) scan. Additional images, such as anterior-posterior, lateral, lateral bending, and standing x-rays, may also be included to add additional information about the deformity. The images may be processed to segment each vertebra into 3D shapes for manipulation. The deformity analysis 224 may include measurements from the images. For example, spinal alignment parameters may be measured from the images either automatically via image processing software or manually by surgeon input. The spinal alignment may be visualized via a curve traced through each vertebra along with lines along medial-lateral features of the vertebra (e.g. transverse process) to visualize rotation. Correction planning 226 may be planned on the images and alignment parameters to achieve the desired correction. The correction may be planned manually by surgeon manipulation of the images, manually by manipulation of alignment parameters which control a curve connecting the vertebrae, or automatic manipulation of alignment parameters to an idealized alignment. Screw placement planning 228 may include pedicle screw placement planning via methods in the robotic navigation platform 20. Beginning of the procedure 230 may occur with patient positioning, anesthesia, and exposure of the spine. Intraoperative navigation and screw placement 232 may include screw navigation and placement performed via methods in the robotic navigation platform 20. Navigated deformity correction 234 may include instruments with fiducial markers rigidly connected to the screws used to track and/or manipulate the spine during correction. These instruments may be manipulated manually or by an electromechanical system. The rigid body motion of the vertebral bodies may be displayed along with the spinal alignment curves to visualize the correction. Real time analysis of the tracked changes in spinal curvature may provide information to the surgeon or feedback to electromechanical control. Completion of the procedure 236 may include capturing and locking of the rods to the screw heads. AP/Lateral images may be taken to confirm correction. Application of bone graft and wound closure may be used to end the procedure.

According to one embodiment, navigation visualization, planning, and intraoperative feedback of deformity correction may include one or more of the following steps. (a) X-ray images may be processed and displayed on touchscreen interfaces via the robotic navigation platform 20. (b) AP, lateral, axial, and plane of maximum curvature may be displayed to visualize the deformity. The 3D images may be panned, rotated, and zoomed. (c) Segmentation of the vertebrae into individual bodies may be done to display their shape instead to clarify the 3D shape of the spine. (d) Sagittal and coronal spinal alignment may be analyzed and visualized via a curve connecting vertebral bodies. Lines parallel to transverse processes, spinous process, or similar anatomy oriented generally perpendicular to the axial plane may be used for analysis of axial rotation. (c) Spinal alignment parameters may be calculated automatically via image processing or manually via surgeon manipulation of the images. (f) Relevant alignment parameters may be found including Cobb angle, lumbar lordosis, thoracic kyphosis, cervical lordosis, axial rotation, sagittal vertical axis, pelvic tilt, pelvic incidence, T1 pelvic angle, 3D kyphosis, and angle of the plane of maximum kyphosis among other measurable alignment characteristics. (g) Correction goals may be defined parametrically by adjusting alignment parameters, by manipulation of 2D images or 3D model of the spine, or automatic adjustment of spinal parameters to an idealized alignment. The corrected spine model may be displayed and adjusted by the surgeon until the desired correction goal is chosen. (h) During intraoperative navigation and correction, the system may track and display the location of vertebral bodies in AP, lateral, axial, and plane of maximum curvature. (i) This tracking is achieved via motion capture of fiducial markers on instruments rigidly attached to pedicle screws embedded in the vertebral bodies. (j) Alignment parameters may be monitored in real time intraoperatively (e.g., coronal Cobb, thoracic kyphosis, axial rotation) via numbers or slider bars to compare current alignment against correction goals. (k) A 2D image or 3D model of the desired correction may be overlaid over the tracked vertebral bodies to observe the translation/rotation required to fully correct the spine. (l) Spinal cord tension may be found. Vertebral foramen shape may be used to estimate tension/compression of the spinal cord. For example, positive displacement between centroids of adjacent vertebral foramen may result in a net tension on the spinal cord. (m) Tension/compression of the spinal cord may be shown to the surgeon in a color map on a spline between vertebral bodies, or as a warning indicator on the robotic navigation platform 20.

Figure 13A:
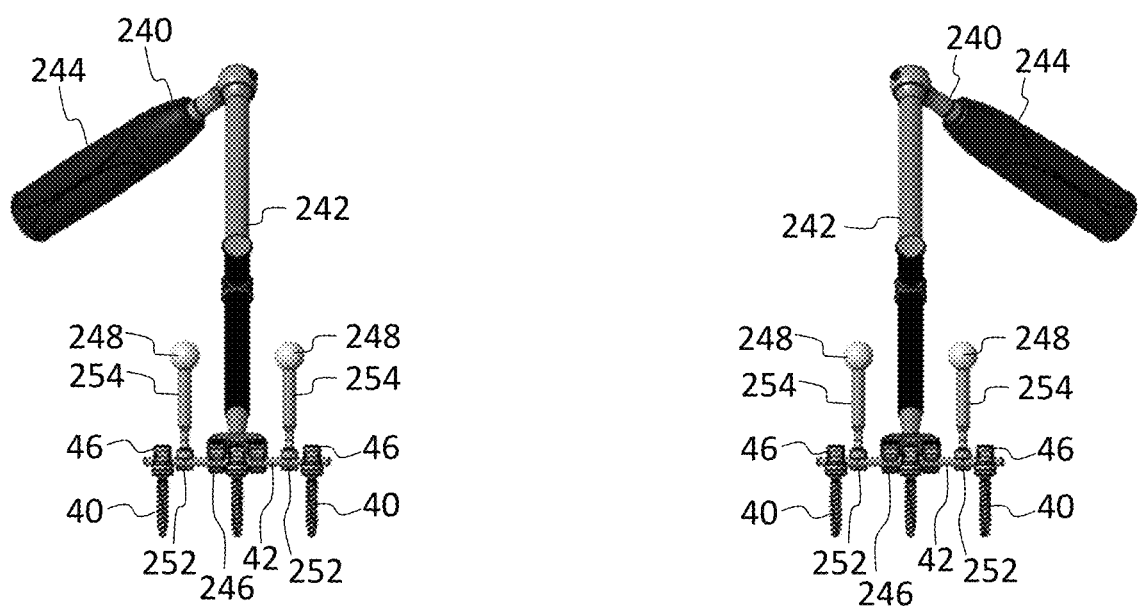
FIGS. 13A-13C show examples of navigated rod link reducers with fiducial markers placed on the temporary spinal rods, a schematic visual representation to display spinal alignment, and locking caps with integrated fiducial markers, respectively.
Figure 13B:
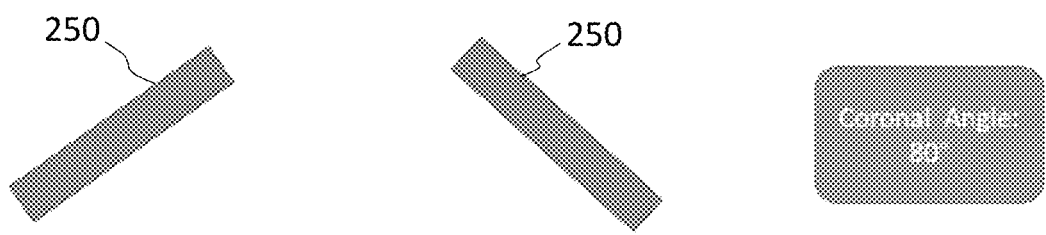
Figure 13C:
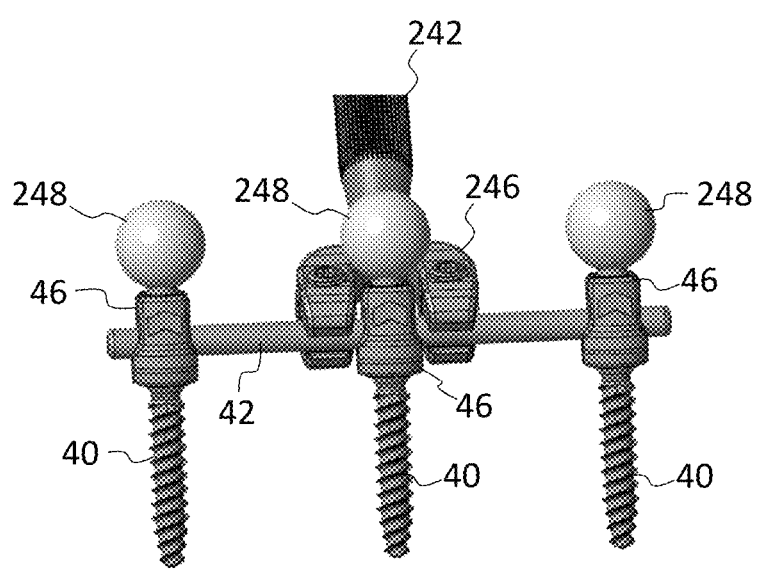

Turning now to FIGS. 13A-13C, systems and methods of intraoperatively tracking the progress of deformity correction using rod link reducer instruments 240 are shown. Rod link reducer 240, similar to rod link reducer 110, includes a manipulating arm or manipulator rod 242 and a handle 244. The distal end 246 of manipulator rod 242 includes a distal tip with a receiver adapted to releasably secure the temporary spinal rod construct therein. Fiducial markers 248 may be attached to the rod link reducer instruments 240, the temporary spinal rods 42, or the pedicle screws 40 to track motion of the vertebrae 2. The robotic navigation system 20 may be used to track the location of the fiducial markers 248 during the procedure and display a schematic representing the anatomical shape of the patient's spine in real time.

In one embodiment, two fiducial markers 248 are placed on each of the temporary rods 42 and one fiducial marker 248 is placed on the spinous process of the vertebrae at the apex of the deformity. As shown in FIG. 13A, the two fiducial markers 248 are placed on each temporary rod 42, which may be tracked to create a line segment 250 at the proximal and distal ends of the deformity. As shown in FIG. 13B, a schematic of possible visual representation used to display spinal alignment is shown. The orientation of the line segments 250 with respect to one another may give a visual representation of the magnitude of the curve in the coronal plane. The line segments 250 may be used to display measurements of applicable spinal parameters, such as coronal Cobb angle. Similarly, the fiducial markers 248 may be used to display a visual representation of the spine's alignment in the sagittal and axial planes.

The fiducial markers 248 may be attached to the temporary rod 42, bone screws 40, and/or rod reducers 240 using a suitable clamp or securing member. In the embodiment shown in FIG. 13A, the fiducial markers 248 are attached to the temporary rods 42 with a clamp 252 and connecting rod 254. The clamp 252 may include a c-clamp or u-clamp, for example, with a set screw to secure the clamp 252 to the spinal rod 42. The connecting rod 254 may extend the fiducial markers 248 vertically above the spinal rods 42. Other embodiments may include fiducial markers 248 which are integrated with or engaged with the locking caps used to secure the temporary rods 42. As shown in FIG. 13C, the fiducial markers 248 may be connected to the tops of the tulip heads 46, for example, with a locking cap having an integrated fiducial marker 248. Alternatively, the fiducial markers 248 may be attached to the manipulating arms 242 or the coupling rod. Additional fiducial markers 248 may be placed on the vertebral segments at the apex of the deformity in order to track motion of the entire spine. These fiducial markers 248 may be secured directly to the anatomy via specialized clamping mechanisms or indirectly by attaching to pedicle screws 40.

In addition to tracking the location and orientation of anatomy via fiducial markers 248, it may be advantageous to monitor the forces exerted on the spine during correction maneuvers. Real time feedback of corrective forces may indicate to the surgeon when screws 40 are at risk of pulling out or plowing. This may allow the surgeon to provide safer correction maneuvers during surgery. In one embodiment, strain gauge sensors are placed on the manipulating arms 242 of the rod link reducer 240. Deflection of the manipulating arms 242 during correction may be sensed by the strain gauge and recorded by the robotic navigation system 20. Increased corrective forces may cause an increased reading from the strain gauge. The robotic navigation system 20 may record, monitor, and display the strain readings to the surgeon as well as give warnings when the strain is increased to unsafe levels. The surgeon may use this data to adjust his correction maneuvers accordingly so as to not risk patient safety. Other embodiments may include placing the strain gauge sensors on the coupling rod, handles, coupling clamps, or temporary rods. Alternatively, strain gauge sensors may be placed on the pedicle screws themselves to directly measure stress at the bone/screw interface. This method may directly monitor when stress is nearing a level where the pedicle screw might plow or pull out.

The rod link reducer instruments 240 are used to manipulate the deformed spine into a corrected state via anchoring points on the convex side of the spine. After the correction is achieved and locked into place, a permanent rod is bent to the appropriate shape and placed on the contralateral side to hold the correction. The rod link reducer instruments 240 are then removed and a second permanent rod is inserted. The permanent rods are meant to hold the spine in a corrected position while the vertebrae fuse, which means it must resist the forces which caused the deformity. These forces often cause the permanent rods to flatten or bend resulting in loss of correction. In order to counteract this, surgeons often over bend the permanent rod before inserting it so that the final shape of the rod after being acted upon by the forces in the spine is closer to the desired shape. This method is called differential rod bending and may be difficult to get correct. Therefore, it may be advantageous to give surgeons relevant data that they may use to make more accurate judgments when it comes to differential rod bending. Furthermore, it may be more advantageous if the relevant data could be used to automatically bend a rod to the appropriate shape that would achieve the desired correction post-operatively.

According to one embodiment, a method of collecting and analyzing relevant pre-operative and intra-operative data may be used to create a permanent rod with the ideal shape for maintaining the desired deformity correction. Pre-operative measurements of clinically relevant variables, such as upper instrumented vertebrae (UIV), lower instrumented vertebrae (LIV), thoracic kyphosis, standing coronal cobb angle, bending coronal cobb angle, and sagittal vertical axis (SVA) are determined using x-ray, CT scan, MRI, or other imaging methods, may be collected. Navigation methods may be used to monitor the position of the spine during surgery and track changes to the clinically relevant variables measured pre-operatively. Strain sensors placed on the rod link reducer instruments or implants or other techniques described herein may be used to measure the forces exerted on the spine during the correction maneuvers. The intra-operative measurement data collected via navigation and the strain gauge sensors is recorded and analyzed by the robotic navigation system 20. After the desired correction is achieved and locked into place using the rod link reducer instruments 240, the position of the contralateral pedicle screws and 3D profile of the spine is collected by the robotic navigation system 20. An algorithm in the robotic navigation system 20 then uses the pre-operative measurements, intra-operative measurements, intra-operative correction forces, pedicle screw locations, and 3D profile to determine the optimal rod shapes. The information is then given to a rod bender machine and the permanent rods are automatically bent to this ideal shape. The surgeon then places the appropriate pre-bent rod on the contralateral side and it is locked into place. The rod link reducer instrumentation 240 is removed and the second pre-bent rod is inserted and locked into place.

The measurements collected pre-operatively and intra-operatively may be used to determine the amount of deflection that will occur to the permanent rod when it is inserted. The algorithm used to determine the optimal rod shape may take into consideration the size and material properties of the rod. The algorithm may also take into consideration other variables that may influence spinal balance including patient height, weight, and bone density. Post-operative measurements and clinical outcomes may be collected and recorded into the robotic navigation system 20 in order to assess the algorithm's performance. These results may be used to teach the machine learning algorithm in order to improve its performance over time.

Osteotomies involve the removal of bone and are often needed during spinal deformity surgery in order to make the spine flexible enough to move into a corrected state. If the spine is not flexible enough to move, then correction maneuvers are difficult and may place excessive stress on the implants. Excessive stress on the implants may result in screw plowing or pullout.

In one embodiment, pre-operative and intra-operative data may be used to determine an ideal rod shape to hold correction. This pre-operative and intra-operative data may also be used to aid the surgeon in deciding when and where to perform osteotomies. The intra-operative strain gauges or force measurements may indicate to the surgeon when the pedicle screws are at risk of pulling out or plowing. If the strain gauges indicate that excessive force is being placed on the pedicle screws during correction then the surgeon knows they need to loosen the spine before continuing with the correction maneuvers. The spine may be loosened by performing osteotomies at strategic levels. Positional tracking of the spine during correction combined with strain or force measurements from the instruments or implants may be used to determine the ideal location and extent of osteotomies. This information may allow the surgeon to minimize the stress placed on the spine during correction.

In yet another embodiment, the rod link reducer 240 may be manipulated and navigated with the robotic navigation system 20. The arms 24 of the robot 22 may be used to manipulate the navigated rod link reducers 110, 240 described herein or a non-navigated rod link reducer. Displacement pathing of the vertebral bodies attached to the manipulating arms 242 may be planned for gradual and controlled correction between the deformed and corrected positions. The end effector 30 may rigidly attach to manipulating arm 242 of the reducer 240. Vision targets on the manipulating arm 242 may be used to align and attach the manipulating arm 242 or the end effector 30 may be guided manually to engagement by the surgeon. In place of fiducial markers on the manipulating arms 242, the active markers on the end effector 30 may be used to track motion of the manipulating arm 242 once engaged. Two serial arm manipulators may be used to simultaneously control both manipulating arms 242 (both systems must communicate & coordinate to eliminate collisions and ensure consistent motion). One serial arm manipulator may be used with the other anchored to a table attachment or held by surgeon. Manipulating arms 242 may be articulated gradually by the robot 22 to correct the deformity. Correction may be initiated by the surgeon by depressing a foot pedal, and paused or stopped by release of the pedal. The load cell in wrist may be used in place of strain gauges on the manipulating arms 242 to monitor corrective forces and moments. Force-displacement data may be used for real time feedback and adjustment of correction pathing. A force threshold or drop in a linear force-displacement curve may be used to prevent implant pullout or loosening of the bone-screw interface. If pullout or loosening is detected motion may be stopped and the spine permitted to relax. Once the force has dropped below a threshold, correction may resume. Pathing may be adjusted to reduce corrective forces, or the amount of correction may be adjusted. The spine may be manipulated to pivot about a center of rotation level with the spinal cord, minimizing stretch or buckling of the cord. Rigid body motion of the vertebral bodies may be tracked to prevent impingement of the cord. An angular displacement may be applied to achieve a specific angle of correction.

According to another embodiment, a screw extender instrument may have fiducial markers built into or added to the instrument. The instrument rigidly attaches to the screw head and aligns with the drive feature of the screw shank to be rigidly coupled to the vertebral body. Fiducial markers attached to reduction, derotation, and screw extender instruments may be used to track rigid body motion of vertebral bodies during reduction and derotation procedures. Screw extender instruments attached to screws on the contralateral side from reduction and derotation instruments may be used to rigidly track the vertebral bodies. Reflective markers/rings mounted to threaded reduction instruments may be used to measure the amount of reduction. Strain gauges attached to the instruments may be used to monitor reduction and derotation loads.

According to another embodiment, the serial arm manipulator of the robotic navigation system 20 may be used to manipulate the navigated reduction and derotation instruments described herein or a standard non-navigated instrument. Displacement pathing may be used to control the center of rotation of the derotation maneuver. This may be used to rotate about a rod, the center of the vertebral body, the center of the canal, or prevent loss of kyphosis during correction. Motion of vertebral bodies may be tracked via the active markers on the end effector if it is rigidly attached to an instrument. Forces and moments may be monitored by the load cell in the wrist to prevent pedicle blowout or loosening of the bone-screw interface.

According to another embodiment, fiducial markers may be built into or added to extended tabs of MIS tulips, screw extender, or other reduction or derotation instruments. An alternative embodiment is an active marker array with infra-red LEDs with variations in position, wavelength, and/or pulse pattern to allow unique identification of the array. They may be a single-use, sterile-packed instrument that is activated via a pull-tab that connects the battery. Each tulip/instrument may have a unique set of locations so that navigation may distinguish between each screw (e.g. T10, Right) so that each screw may be simultaneously tracked. The fiducial markers may be used with a screwdriver array or screw extender for navigation.

According to another embodiment, correction planning described herein may be used to estimate the degree of forces required to correct the spine. The trajectory, diameter, and length of a pedicle screw may be adjusted to improve resistance to loosening of the bone-screw interface in a specific loading condition. For example, a screw anticipated to undergo more sagittal reduction than coronal reduction may be placed to improve its pullout strength in the posterior direction over loosening in the lateral direction. A finite element model may be used with varying loading conditions, screw trajectories, and dimensions in an optimization study.

Figure 14:
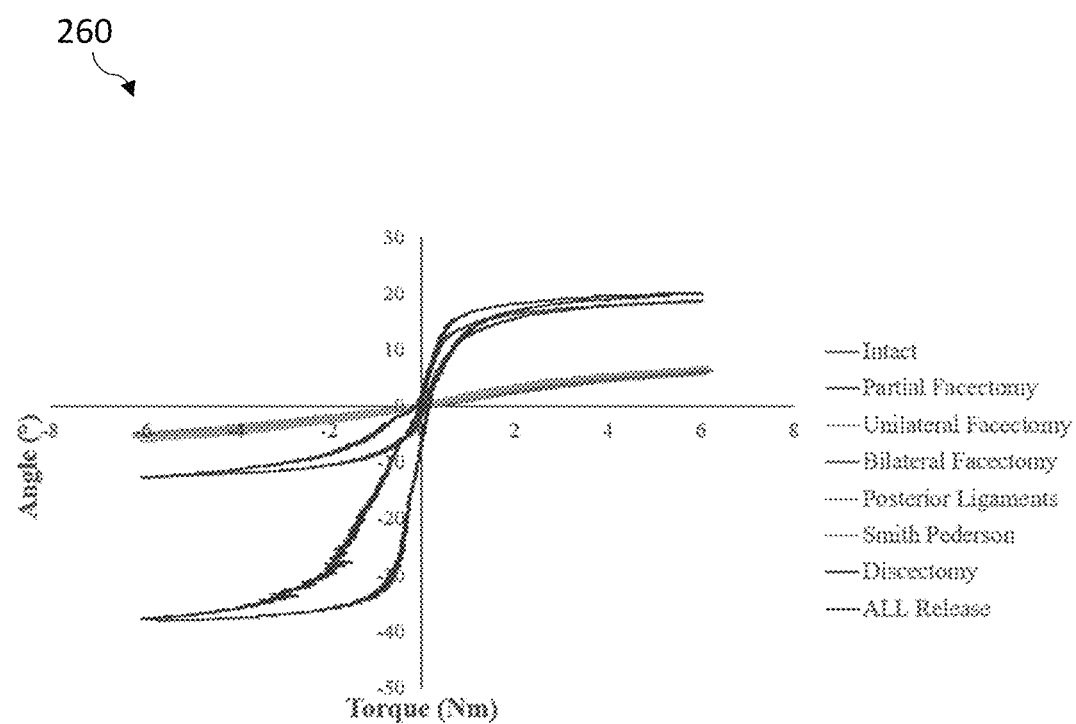
FIG. 14 is a kinematic model showing a known torque and outputs an angulation after the torque is applied for various procedures.

Turning now to FIG. 14, a kinematic model 260 outputs the expected apparent force on bone-implant (screw, sublaminar band, spinous-process band/clamp, hook, or expandable/static interbody spacer) interface during planned correction maneuvers, and the likelihood of attaining desired alignment prior to bone-implant interface failure. Biomechanical cadaveric training data for kinematic model 260 is trained via cadaveric tissue resections of various constraining vertebral body anatomy (Schwab 1-6 osteotomy criteria). 6DOF testing machine applies a known torque and outputs an angulation after the torque is applied. Spinal elements including disc, ligaments, and bone are converted to spring elements or rigid bodies of known geometry. Instrument manipulation via assumed static fixation points attached to rigid bone anatomy results in a series of linear algebraic equations that result in a determined movement of the bone anatomy from a pre-surgical orientation to a post-surgical orientation.

Clinical data inputs into kinematic model 260 includes force measurements captured intra-operatively by force-sensing and optically navigated correction instruments and individual vertebral bodies provide additional feedback training to the model 260. Intra-operative data may include surgeon confirmation of completed technique (bone resection, ligamentous resection, discectomy, interbody placement, or various instrument manipulations) via interaction with robotic or augmented reality (AR) interface, navigated movement of cutting tools (osteotomy/ligamentous release/discectomy), compressor/distractor tool with force sensors, rod-link reducer with force sensor, clip reducer with force sensor, lamina spreader with force sensor, or torque-measuring instrument attached to drivers that actuate the clip reducer mechanism or interbody-expansion mechanisms. Indexed intra-operative force measurement and spinal excursion data iteratively improves the kinematic model and its ability to predict apparent force on the implant-bone interface.

Figure 15:
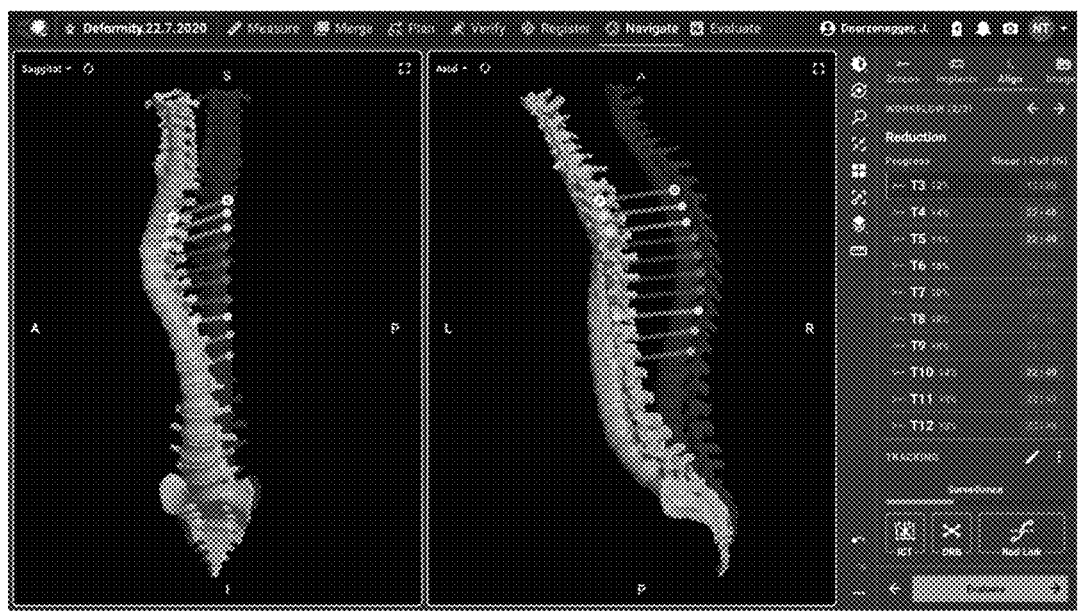
FIG. 15 is an example of a display with sagittal and axial views of the spine and a user interface to plan correction of a spinal deformity.

Kinematic model 260 may takes inputs of various planning parameters by the user including: (1) applied bone/tissue resection; (2) pre- and post-correction alignment (sagittal, axial, and coronal curvature of the spine) via autosegmentation of images; (3) planned instrumentation (screw size, length, trajectory, and type (fenestrated/cemented, HA coated), interbody placement, other fixation placement); (4) planned correction—use correction tool to move spine from point A—point B (e.g., use rod link reducer to move spine from point A-B as seen in FIG. 15). Kinematic model 260 outputs the forces that are required to be applied to the spine in order to move from point A to point B with a prescribed correction maneuver. Kinematic model 260 may incorporate bone-implant interface failure model to predict whether the forces required to move the spine from point A to point B are too great and may result in a bone-implant interface failure. The failure likelihood may be relayed to the surgeon in a color-coded fashion in the image shown in FIG. 15.

Figure 16:
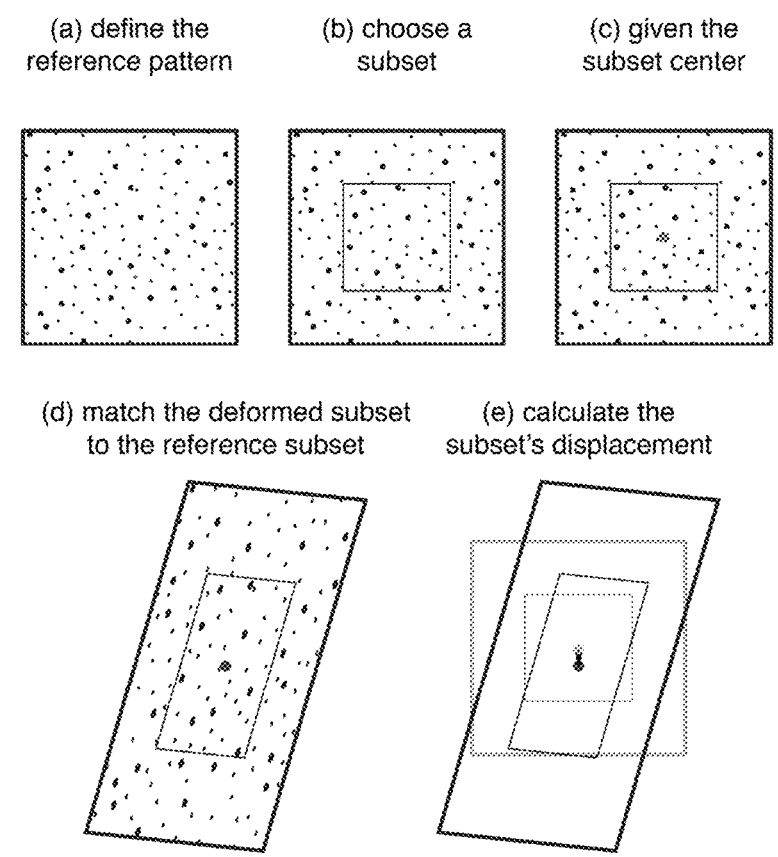
FIG. 16 is a digital image correlation process according to one embodiment.

Turning now to FIG. 16, digital image correlation process 270 is shown according to one embodiment. Digital image correlation 270 may be used to determine an optical force measurement on rod link reducer manipulating arms, clip reducers, compressor/distractor, or other deformity correction instruments. The process may include (a) defining the reference pattern; (b) choosing a subset; (c) given the subset center; (d) matching the deformed subset to the reference subset; and (e) calculating the subset's displacement. Cameras on an augmented reality headset or the robotic navigation system 20 may be used to capture the pixel pattern under no load prior to administration of correction. During the correction maneuver, cameras may be trained on the pixel pattern, and as the subset displacement occurs, software translates the deformed subset geometry into a 3-dimension force vector. This instrument force vector may then be transformed via software into an apparent force on the bone-implant interface calculated in software as an apparent force on the bone-implant interface. The apparent force on the bone-implant interface may be color coded to relay risk of bone-implant interface failure.

During correction maneuvers, pedicle screws may pull-out of the pedicle or they may breach the medial or lateral wall of the pedicle by plowing. Factors contributing to pull-out or breach include the quality of bone, the location of placement of the screw in bone, the morphology of bone, the size and length of the pedicle, the size and length of the bone anchor/pedicle screw, the trajectory of the pedicle screw, and the forces applied to the pedicle screw.

According to another embodiment, a fixation strength model may be created via various inputs including screw-insertion torque from a torque-indicating screwdriver, screw size and placement trajectory via robotic or navigated placement of screws, pedicle morphology information via autosegmentation software applied to a CT/MRI scan, opportunistic bone density measurements via radiograph (CT, EOS, MRI), bone density measurement from microindentation (applying a pin of known force and measuring the resultant microindentation) and medical data (drug intake, age, prior medical history, gender, hormonal status etc.).

Post-implant placement, additional datapoints may be collected on fixation strength by applying a radio frequency (RF) through the screw and measuring the resultant RF frequency that is emitted through the bone, indicating both density of the material through which the RF wave travels and the interface surface area between the bone and implant. A multivariate or machine learning model uses various datapoints described above and clinical data collected during surgery to predict the force at which a failure occurs at the bone-implant interface. Implant-bone interface failure may occur with expandable interbodies via breaking through endplates above or below, or at the screw/hook-bone interface via shearing, pulling, or otherwise translating the fixation point relative to the bone. Every occurrence of this implant-bone interface failure may be recorded during surgery and used as a recursive datapoint for improving the predictive model.

According to another embodiment, vertebral body tracking may use the following steps. Input to machine learning auto-segmentation model may include CT/MRI/biplanar x-ray/ultrasound or other imaging modality. The following algorithms may be used for contour extraction—Topological Structural Analysis of Digitized Binary Images by Border Following (2D), Deep Neural Network (2D), Deep Neural Network (3D), Image segmentation (Watershed), or Image segmentation (Superpixels). The following algorithms may be used for 3D reconstruction—Grid-based meshing, Screened Poisson Surface Reconstruction (Screened PSR), Smooth Signed Distance Surface Reconstruction (SSD), Visibility based Surface Reconstruction, or Gaussian Process Morphable Models. After 3D reconstruction is performed for individual vertebral bodies, the model is used in robotics/navigation workflows. Navigated placement of screws may provide a precise location of the screw in the 3D reconstructed vertebral body CAD model. The screw location with an attached tracking array may then mark the location of individual vertebral bodies. Location of individual vertebral bodies relative to one another may be outputted to the user in the form of global alignment data (coronal cobb angle, CSVA, C7PL, lumbar lordosis, thoracic kyphosis) or segmental data (disc height, segmental lordosis, foraminal height)

According to another embodiment, preoperative radiographic parameters including subarticular diameter, central canal diameter, central canal area, foraminal height, foraminal area, segmental lordosis, and disc height may be extracted from autosegmentation software described above. Radiographic parameters may change in response to inserted interbody or navigated cutting instrument. Collected post-operative patient reported outcomes may label the change in radiographic parameters as successful or not-successful at various time points. The model may incorporate either intra-operative navigated changes in radiographic parameters, or post-operatively collected radiographs. Multi-variate model incorporating resultant change in radiographic parameters may determine likelihood of decompression failure. Intra-operatively, this likelihood of decompression failure may be displayed to the surgeon, indicating what end alignment or direct decompression maneuver (bone/ligament removal) is useful for a higher likelihood of successful outcome.

The devices, systems, and methods described herein may improve the safety, efficacy, reliability, and/or repeatability of correction maneuvers during deformity surgery. Leveraging the technological advancements in robotics and navigation may give surgeons patient specific data they may use to optimize clinical outcomes. These approaches have the potential to give surgeons more information so they may make better decisions during surgery. This information may be aggregated into a database and utilized to create and improve algorithms for predicting, tracking, and achieving optimal deformity correction and/or may be used to raise the standard of care for patients.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all components of the various devices disclosed above may be combined or modified in any suitable configuration.

What is claimed is:

1. A trackable instrument for correcting a spinal deformity comprising:
    a body having a distal portion configured to perform a surgical task and a proximal portion configured to be manipulated by a user,
    a plurality of markers configured to be tracked by a navigation system including a rigid marker and a movable marker attached to the body;
    a flexible portion located along the body, wherein the flexible portion is positioned between the rigid marker and the movable marker, and
    wherein when the surgical task is performed, the plurality of markers indicate an amount of force applied to the instrument.

2. The trackable instrument of claim 1, wherein the instrument is further configured to characterize a stiffness of a spine by measuring navigated displacements of the spine resulting from applied forces by the instrument.

3. The trackable instrument of claim 1, wherein the surgical task is compression, distraction, reduction, and/or derotation of a spine.

4. The trackable instrument of claim 1, wherein the flexible portion has a known stiffness, relative motion of the movable marker relative to the rigid marker results from the known stiffness of the flexible portion, and the relative motion is measurable by the navigation system.

5. The trackable instrument of claim 1, wherein the flexible portion includes one or more relief cuts, a reduced segment having a reduced width, or a flexible material section.

6. The trackable instrument of claim 1, wherein the flexible portion includes one or more relief cuts having linear or helical cuts.

7. The trackable instrument of claim 1, wherein the flexible portion includes linear relief cuts, a decreased width, and a helical cut, thereby resulting in decreased stiffnesses in different directions due to varying orientations of removed material.

8. A system for correcting a spinal deformity comprising:
    a navigation system including an infrared signal based position recognition system; and
    a trackable instrument having a plurality of markers viewable and trackable by the navigation system, the plurality of markers including a rigid marker and a movable marker attached to the instrument, the trackable instrument includes a flexible portion having a known stiffness, wherein the flexible portion is located between the rigid marker and the movable marker, and wherein relative motion of the movable marker relative to the rigid marker results from the stiffness of the flexible portion, and the relative motion is measurable by the navigation system.

9. The system of claim 8, wherein the trackable instrument is a compressor, distractor, reducer, or derotator.

10. The system of claim 8, wherein the trackable instrument is a compressor or distractor having a first pivoting arm and an opposed second pivoting arm interconnected at a center pivot pin, the first and second pivoting arms each define a handle, the flexible portion is defined in one of the handles above the pivot pin, the rigid marker is affixed to a rigid segment of the first or second pivoting arm, and the movable marker is affixed to one handle on an opposite side of the flexible portion.

11. The system of claim 10, wherein a first rigid marker is attached to the first pivoting arm below the center pivot pin, a second rigid marker is attached to the second pivoting arm above the center pivot pin on one side of the instrument, and the movable marker is attached to the handle via a lever arm on an opposite side of the instrument.

12. The system of claim 8, wherein the trackable instrument is a rod link reducer having a manipulator arm and a handle, the flexible portion is defined into the manipulator arm, a proximal array including the movable marker is located proximally and a distal array including a rigid marker is located distally along the manipulator arm, and the flexible portion separates the distal array from the proximal array.

13. The system of claim 8, wherein the trackable instrument is a rib pusher having a body handle defining a hollow interior, a plunger having a piston received in one end of the body handle, and a spring located inside the body handle, the rigid marker is located on the body handle, and the movable marker is located on the plunger.

14. The system of claim 8, wherein the trackable instrument is a reducer having a body, a pair of engagement tabs attached to the body, and a central pusher threaded through the body, the rigid marker is located on the body, and the movable marker is located on the engagement tab.

15. The system of claim 14, wherein each engagement tab has a proximal section and a distal section that terminates at a free end configured to engage a screw head, the engagement tab is attached to the body at a connecting portion adjacent to a flexure, and when tension is applied to the engagement tab during reduction or derotation, the proximal section acts as an extended moment arm, and extends off of the flexure to magnify displacement of the movable marker.

16. A trackable instrument for correcting a spinal deformity comprising:
    a body having a distal portion configured to perform a surgical task and a proximal portion configured to be manipulated by a user,
    a plurality of markers configured to be tracked by a navigation system including a rigid marker and a movable marker attached to the body;
    a flexible portion located along the body, wherein the flexible portion is positioned between the rigid marker and the movable marker, and
    wherein when the surgical task is performed, when the surgical task is performed, a change in the relative position of the plurality of markers indicates an amount of force applied to the instrument.

17. The trackable instrument of claim 16, wherein the instrument is further configured to characterize a stiffness of a spine by measuring navigated displacements of the spine resulting from applied forces by the instrument.

18. The trackable instrument of claim 16, wherein the surgical task is compression, distraction, reduction, and/or derotation of a spine.

19. The trackable instrument of claim 16, wherein the flexible portion has a known stiffness, relative motion of the movable marker relative to the rigid marker results from the known stiffness of the flexible portion, and the relative motion is measurable by the navigation system.

20. The trackable instrument of claim 16, wherein the flexible portion includes one or more relief cuts, a reduced segment having a reduced width, or a flexible material section.

* * * * *